(12) United States Patent
Minemura et al.

(10) Patent No.: US 10,041,874 B2
(45) Date of Patent: Aug. 7, 2018

(54) OPTICAL MEASUREMENT METHOD AND APPARTUS

(71) Applicant: Hitachi-LG Data Storage, Inc., Tokyo (JP)

(72) Inventors: Hiroyuki Minemura, Tokyo (JP); Kentaro Osawa, Tokyo (JP); Yumiko Anzai, Tokyo (JP)

(73) Assignee: Hitachi-LG Data Storage, Inc., Tokyo (JP)

( * ) Notice: Subject to any disclaimer, the term of this patent is extended or adjusted under 35 U.S.C. 154(b) by 0 days.

(21) Appl. No.: 15/351,556

(22) Filed: Nov. 15, 2016

(65) Prior Publication Data

US 2017/0160185 A1 Jun. 8, 2017

(30) Foreign Application Priority Data

Dec. 2, 2015 (JP) .................................. 2015-235980

(51) Int. Cl.
| | |
|---|---|
| *G01N 15/02* | (2006.01) |
| *G01N 15/14* | (2006.01) |
| *G01B 9/02* | (2006.01) |
| *G01N 15/10* | (2006.01) |

(52) U.S. Cl.
CPC .......... *G01N 15/14* (2013.01); *G01B 9/02041* (2013.01); *G01B 9/02091* (2013.01); *G01N 2015/1006* (2013.01); *G01N 2015/1493* (2013.01)

(58) Field of Classification Search
CPC ............ G01B 9/02041; G01B 9/02091; G01N 15/14; G01N 2015/1006; G01N 2015/1493
See application file for complete search history.

(56) References Cited

U.S. PATENT DOCUMENTS

| | | |
|---|---|---|
| 2014/0152978 A1 | 6/2014 | Carr et al. |
| 2014/0204388 A1 | 7/2014 | Osawa et al. |

*Primary Examiner* — Tri T Ton
(74) *Attorney, Agent, or Firm* — Mattingly & Malur, PC

(57) ABSTRACT

An objective of the present invention is to provide a technique for reducing measurement errors when measuring specimen using light. An aspect of an optical measurement method according to the present invention: acquires relationship data that describes a relationship between an intensity of reflection light when irradiating light onto a specimen and a size of the specimen; and acquires the size of the specimen using the relationship data and the intensity of the reflection light. Another aspect of an optical measurement method according to the present invention subtracts a component due to an inclination of a vessel of a specimen from a detection signal representing an intensity of reflection light when irradiating light onto the specimen, thereby correcting the inclination of the vessel.

4 Claims, 22 Drawing Sheets

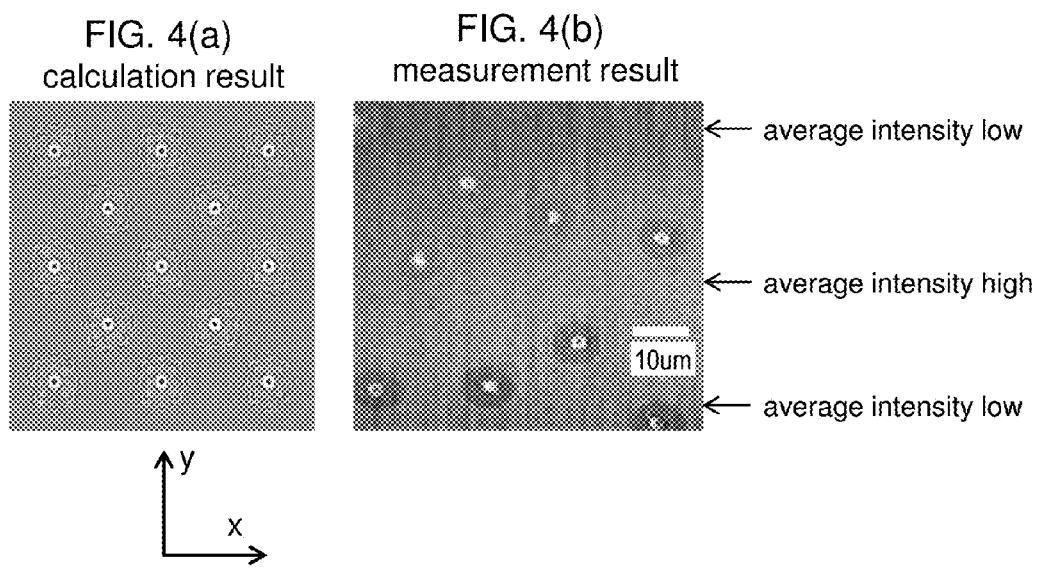
FIG. 4(a) calculation result
FIG. 4(b) measurement result
← average intensity low
← average intensity high
← average intensity low
FIG. 5
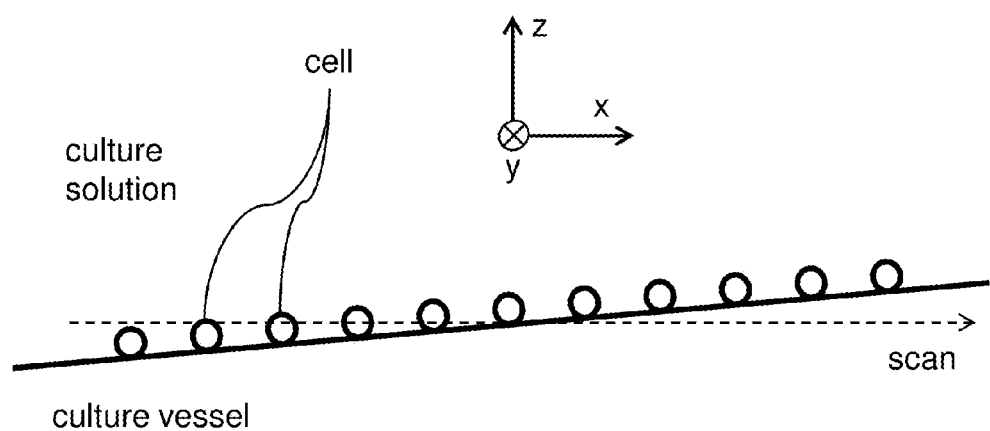

FIG. 9(a)
calculation result
Image(x,y)
FIG. 9(b)
processing result
Image2(x,y)
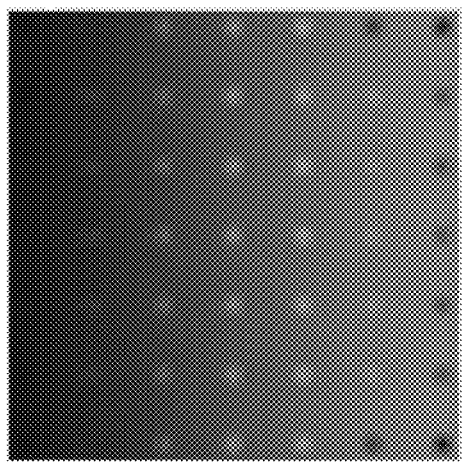
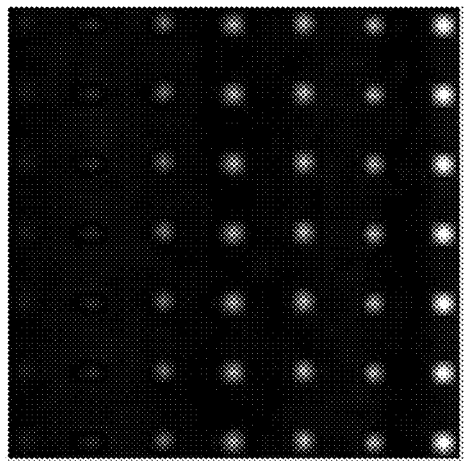
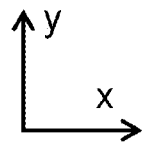

FIG. 11(a)
calculation result
Image(x,y)
FIG. 11(b)
processing result
Image2(x,y)
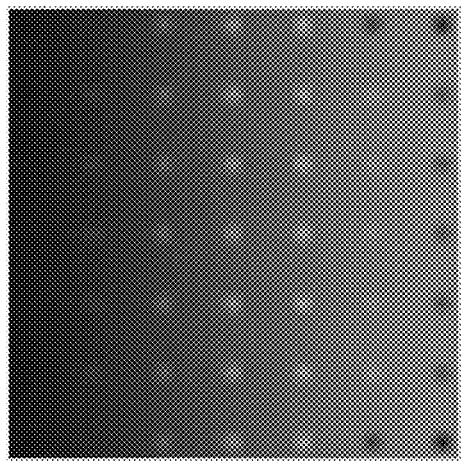
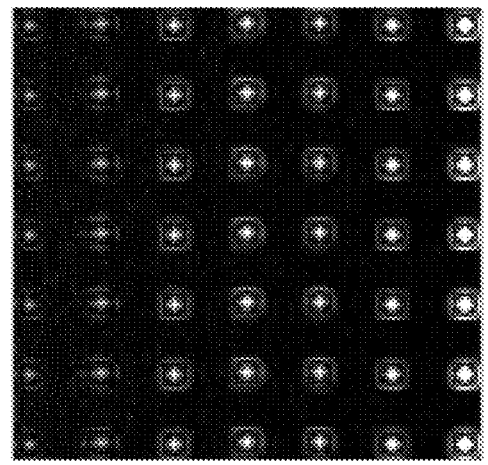
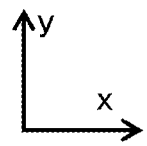
FIG. 12
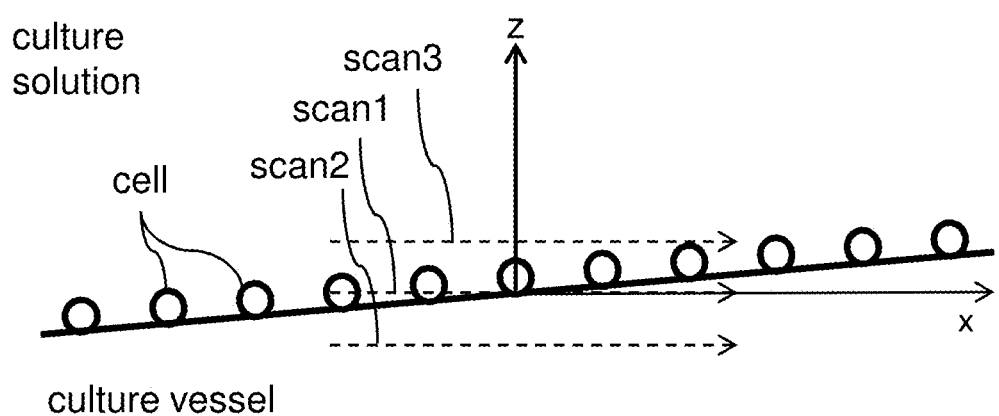

FIG. 15(a)
calculation result
Image(x,y)
FIG. 15(b)
processing result
Image2(x,y)
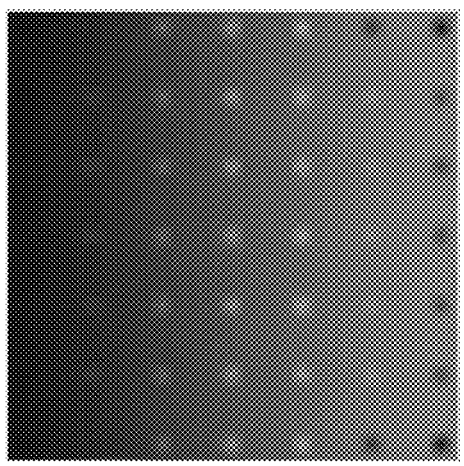
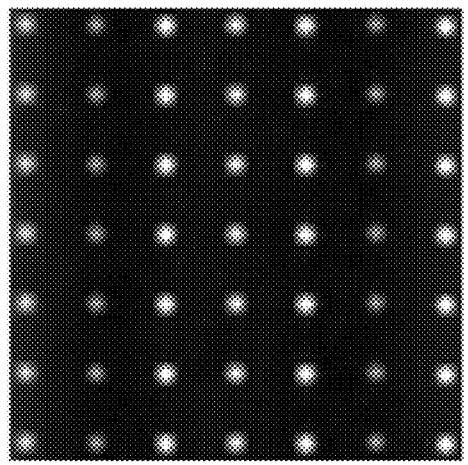
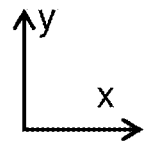

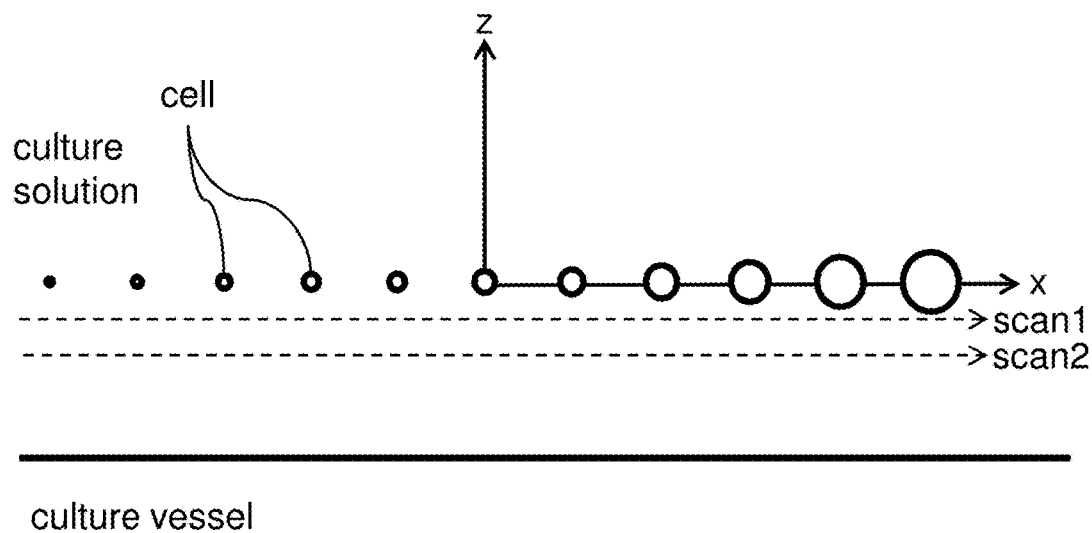
FIG. 16(a) calculation model
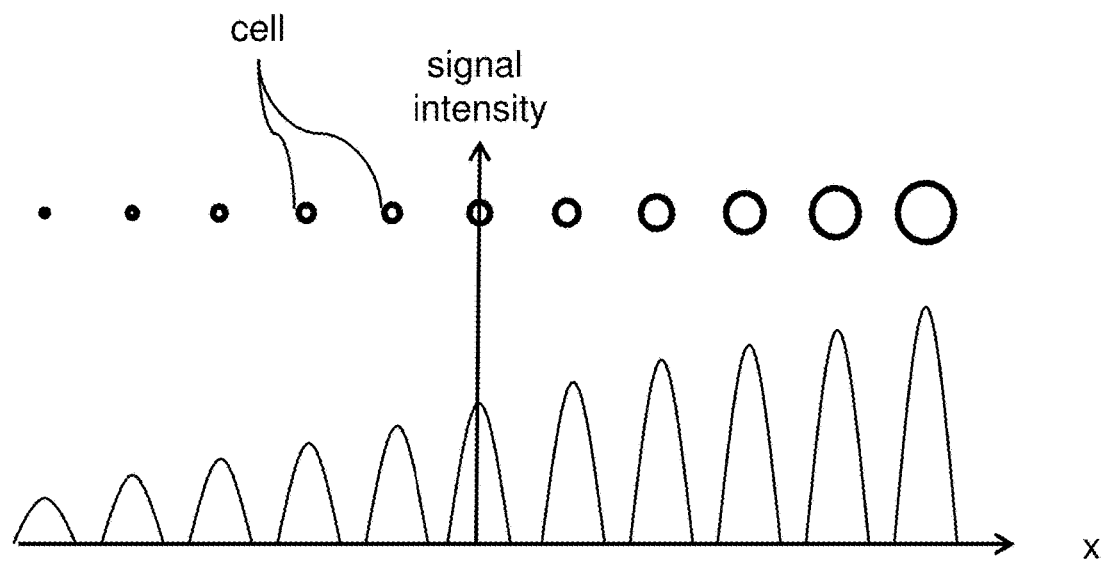
FIG. 16(b) schematic diagram of signal FIG. 19(a) zFP=0um
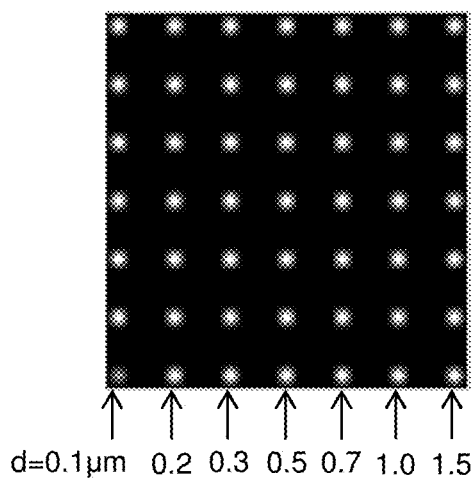
d=0.1µm 0.2 0.3 0.5 0.7 1.0 1.5
FIG. 19(d) zFP=-0.5um
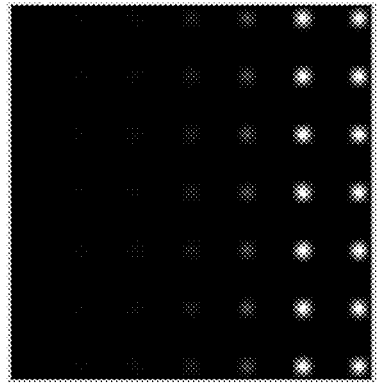
FIG. 19(b) zFP=-0.1um
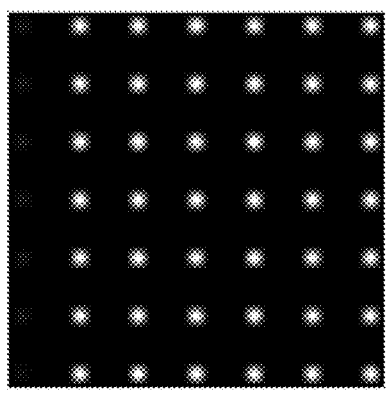
FIG. 19(e) zFP=-1.0um
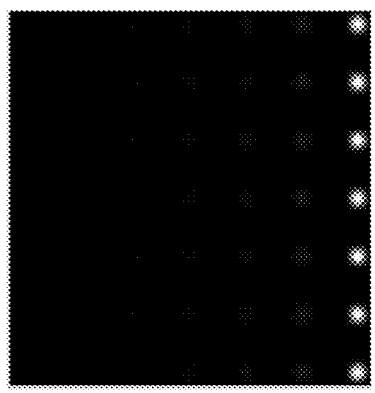
FIG. 19(c) zFP=-0.2um
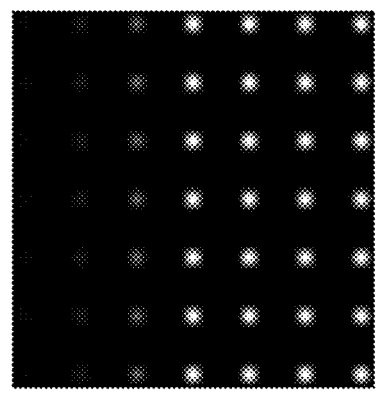
FIG. 19(f) zFP=-1.5um
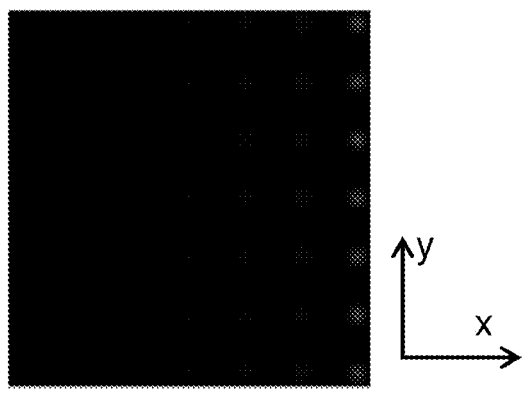

FIG. 20(a) cell is small          FIG. 20(b) cell is large
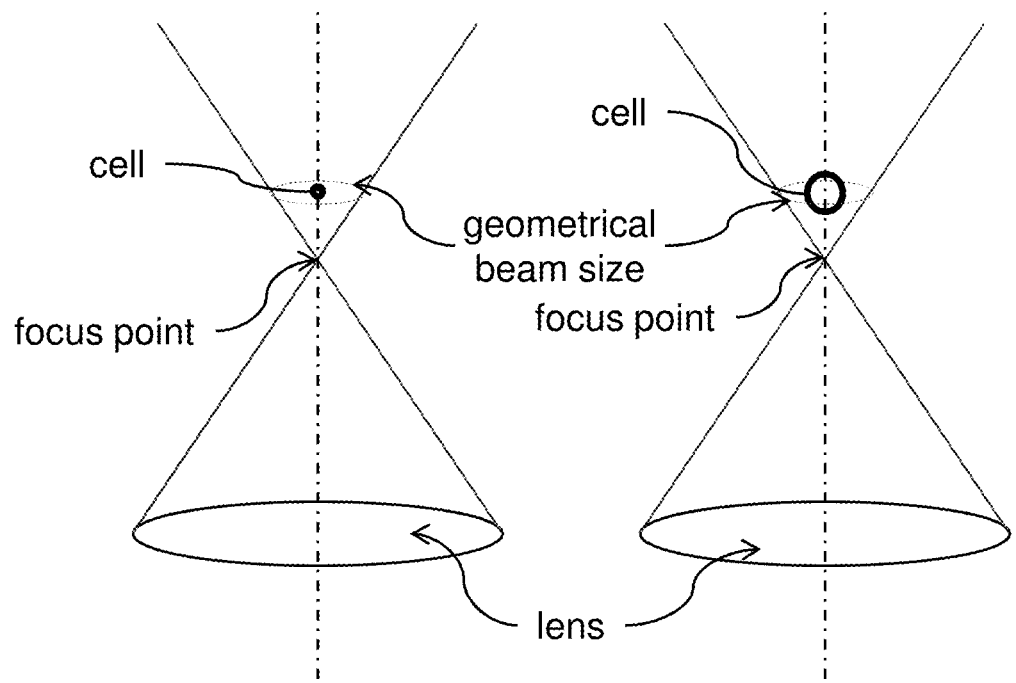
FIG. 20(c) defocus and detection signal
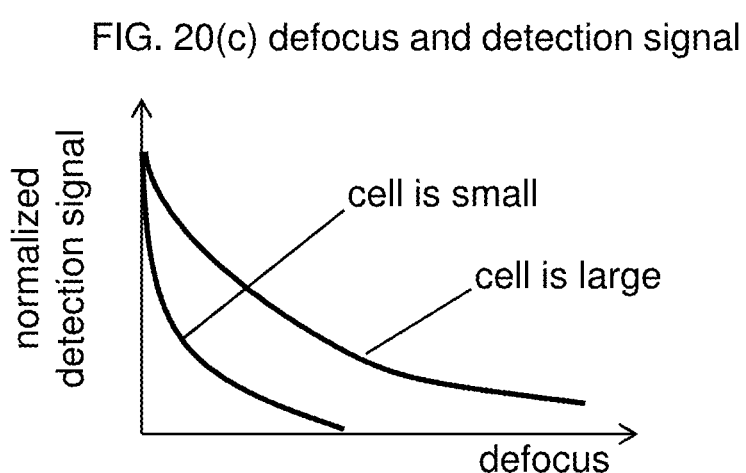

OPTICAL MEASUREMENT METHOD AND APPARTUS

CLAIM OF PRIORITY

The present application claims priority from Japanese patent application JP 2015-235980 filed on Dec. 2, 2015, the content of which is hereby incorporated by reference into this application.

BACKGROUND

Technical Field

The present invention relates to a technique for measuring specimens using light.

Background Art

In recent years, Optical Coherence Tomography, which acquires using light images in which surficial structures or internal structures of specimen are reflected, is drawing attentions. Since OCT is not invasive to human bodies, it is expected to be applied to medical fields and biological fields. With regard to ophthalmology fields, devices that form images of ocular fundus or cornea are in practical use. In OCT measurement, light from optical source is divided into signal light and reference light, the signal light acquired by irradiating the light onto the specimen and the reference light acquired by reflecting the light with reference light mirror without irradiating onto the specimen. The signal light reflected from the specimen is multiplexed with the reference light, thereby causing interference with each other to acquire detection signals.

OCT is generally categorized into time domain OCT and Fourier domain OCT depending on the scanning method in the optical axis direction at the measurement position. In time domain OCT, low coherence light source is used as the light source. Scanning is performed in the optical axis direction by scanning the reference light mirror during measurement. Then only the components in the signal light which optical path length is identical to that of the reference light interfere. Signals are demodulated by performing envelope demodulation to the acquired interference signals. On the other hand, Fourier domain OCT is further categorized into swept source OCT and spectrum domain OCT. In swept source OCT, swept source optical source is used that is capable of scanning the wavelength of the emitted light. Scanning in the optical axis direction is performed by scanning the wavelength during measurement. Signals are demodulated by performing Fourier conversion to wavelength dependency (interference spectrum) of the detected interference light intensity. In spectrum domain OCT, broadband light source is used. The generated interference light is dispersed by spectroscope. Scanning in the optical axis direction corresponds to detecting interference light intensity (interference spectrum) for each wavelength component. Signals are demodulated by performing Fourier conversion to the acquired interference spectrum.

Patent Document 1 listed below describes a technique in which the objective lens is physically scanned and in which four detectors each having different phase conditions receive interferences between signal light and interference light, thereby eliminating the need for adjusting phases of reference light by scanning mirrors in time domain OCT.

Patent Document 2 listed below describes a technique that measures, applying scatter angle distribution of protein sample and particle tracking with microscope observation, particle size distribution of sample in conjunction with measurement result of positional disturbance due to Brownian motion.

RELATED ART DOCUMENTS

Patent Documents

Patent Document 1: US2014/0204388
Patent Document 2: US2014/0152978

SUMMARY

Types of biological tissue that can be measured by OCT include: cells; tissues; and aggregate of protein produced by cell. Measured parameters include: macroscopic tissue structure of biological sample that varies depending on such as health state; and number or size of cell, or number or size of aggregate of protein produced by cell, that varies depending on cultural condition. Hereinafter, cell, tissue, and aggregate of protein generated by cell, which are observation targets, are referred to as "cell". Technical descriptions below exemplify measurement of such as number or size of cell, or number or size of aggregate of protein produced by cell, that varies depending on cultural condition.

In general, the size of cultured cell is smaller than wavelength of visible to infrared laser light which wavelength range is highly transmissive to those specimens. The wavelength range is referred to as biological window. Therefore, as described in Patent Document 2, those sizes are measured by performing maximum likelihood estimation to optical measurement result of scatter angle distribution and of particle diffusion.

Well-known Mie scatter theory is employed as the theory for addressing scatter angle distribution. The theory addresses cases where the optical refractive index of the specimen is known in advance and where the particle size of the specimen is approximately larger than the wavelength. Therefore, for example, the theory includes a technical problem that the measurement error may be large in cases where the particle size of the specimen distributes across wide range.

Now a case is assumed where: fluorescent molecules are attached to cells; excited laser light is irradiated onto the cell; fluorescence emitted from the fluorescent molecule is imaged with microscope; image processing is performed to perform particle tracking and analysis, thereby measuring fluctuation of temporal position of individual particles due to Brownian motion. In such a case, Stokes-Einstein equation is used as theoretical background to estimate hydrodynamic sizes. In order to precisely estimate positional fluctuations of individual particles, many pieces of measurement data are required regarding individual specimens, which elongates measurement time. In addition, in order to observe cells smaller than laser wavelength, a preprocessing is necessary to attach fluorescent molecules to observed cells. It raises a technical problem that processing time, reagent costs, and changes in cell state depending on the preprocessing condition (specifically changes in size of aggregated protein) vary, which affect on the measurement result to cause measurement errors.

Further, when measuring cells using OCT, the reflected light from the specimen is much smaller than the reflected light generated at the boundary between the specimen and the culture vessel. In measurement using OCT, image information is acquired by causing interference between the sum of those reflected light and the reference light. Thus the reflected light generated at the boundary (hereinafter, boundary reflection light) behave as noise or crosstalk against measurement of internal reflection light of the specimen. Such boundary reflection light is unnecessary components that decrease measurement accuracy. Such decrease in measurement accuracy due to boundary reflection light causes variations of measured values for number or size concentration of cells.

The present invention is made for solving the technical problems described above. The objective of the present invention is to provide a technique for reducing measurement errors when measuring specimen using light.

An optical measurement method according to the present invention: acquires relationship data that describes a relationship between an intensity of reflection light when irradiating light onto a specimen and a size of the specimen; and acquires the size of the specimen using the relationship data and the intensity of the reflection light.

An optical measurement method according to the present invention subtracts a component due to an inclination of a vessel of a specimen from a detection signal representing an intensity of reflection light when irradiating light onto the specimen, thereby correcting the inclination of the vessel.

With the present invention, it is possible to effectively decrease factors that reduce measurement accuracy when measuring a specimen using light, thereby improving measurement accuracy. Technical problems, configurations, and effects other than mentioned above will be apparent from the descriptions of embodiments below.

BRIEF DESCRIPTION OF THE DRAWINGS

FIG. 4($a$) and FIG. 4($b$) are examples of xy images comparing a simulation result for xy images with a measurement result by an OCT device, respectively.

FIG. 5 is a calculation model in a case where cells are adhered to a boundary of the culture vessel.

FIG. 9($a$) and FIG. 9($b$) are examples of xy images respectively illustrating a simulation result of a detection signal and a result where the measurement method according to the embodiment 1 is performed.

FIG. 11($a$) and FIG. 11($b$) are examples of xy images respectively illustrating a simulation result of a detection signal and a result where the measurement method according to the embodiment 2 is performed.

FIG. 12 is another calculation model in a case where cells are adhered to a boundary of the culture vessel.

FIG. 15($a$) and FIG. 15($b$) are examples of xy images respectively illustrating a simulation result of a detection signal and a result where the measurement method according to the embodiment 3 is performed.

FIG. 16($a$) and FIG. 16($b$) are schematic diagrams respectively illustrating a calculation model in a case where a plurality of cells with different sizes are placed at positions sufficiently away from the boundary of the culture vessel.

FIGS. 19($a$) to FIG. 9($f$) are simulation results respectively illustrating a two dimensional observation image acquired by performing an xy scan to cells with different sizes while changing the focus position.

FIGS. 20($a$) to FIG. 20($c$) are schematic diagrams respectively illustrating a relationship between defocus, detection signal, and cell size.

DETAILED DESCRIPTION

<Embodiment 1: Influence of Boundary Reflection Light>

In order to facilitate understanding of the present invention, decrease in measurement accuracy due to influence of boundary reflection light will be described before describing an embodiment 1 of the present invention. In order to quantitatively describe various effects of the present invention, a calculation method will be used in which interference effect is added to ray tracing (hereinafter, wave-like ray tracing). At the same time, accuracy of wave-like ray tracing will be discussed by comparing with experimental results. Then a configuration of the embodiment 1 of the present invention will be described.

Figure 1:
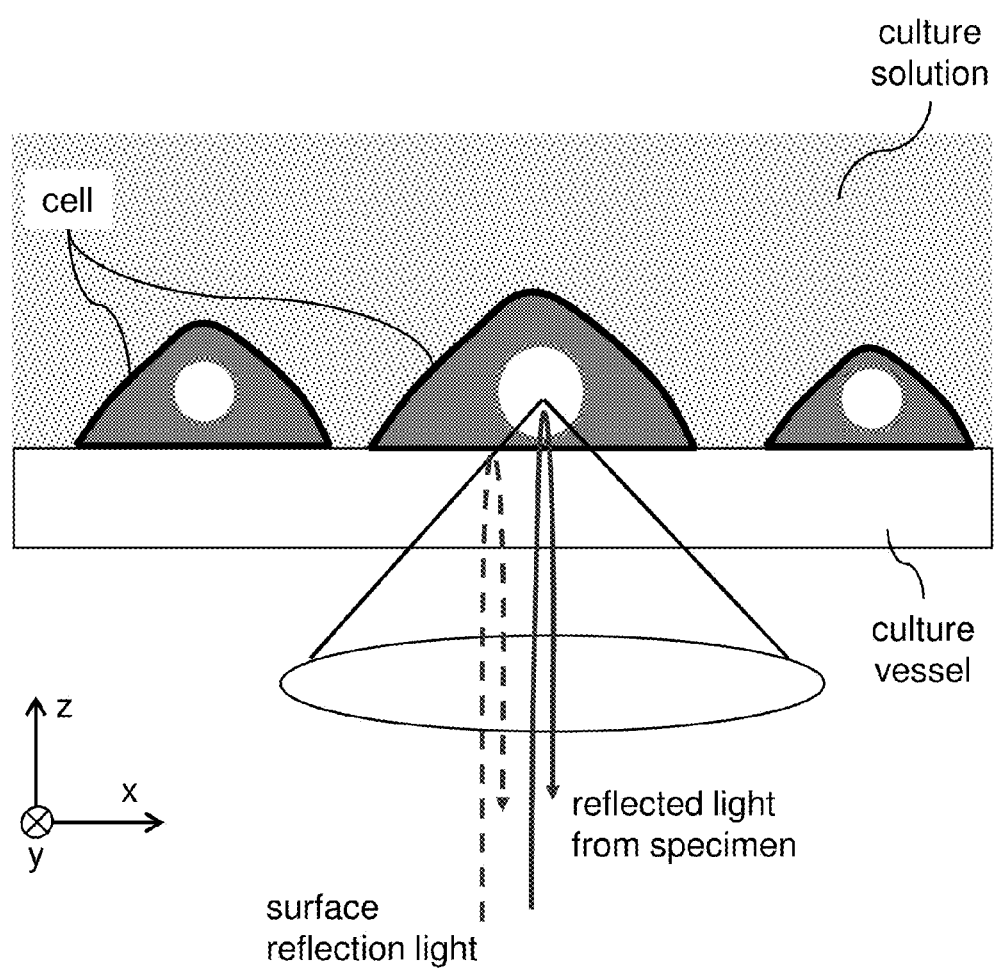
FIG. 1 is a schematic diagram illustrating a scene where a cell is measured that is cultured in a transparent vessel filled with culture solution.

FIG. 1 is a schematic diagram illustrating a scene where a cell is measured that is cultured in a transparent vessel filled with culture solution. Assuming that a refractive index of the culture solution is 1.33 and a refractive index of the cell is 1.38, a reflection index of the cell nucleus is about 0.034% according to Fresnel equation. On the other hand, assuming that a refractive index of typical culture vessel is 1.59, a reflection index is 0.79% at the boundary between the culture vessel and the culture solution or the cytoplasm. Thus it is understood that unnecessary light with intensity greater by more than single digit is generated as boundary reflection light. In actual situation, the cell has a three dimensional structure. Thus the signal light is dispersedly reflected depending on the surface shape. Therefore, less than 0.034% of the light reflected by a single cell is detected as signal light, which further increases influence of the boundary reflection light.

Hereinafter, as described in figures, descriptions will be provided assuming that the optical axis direction is set as the z axis.

In general, a detection signal S acquired by OCT may be described with Equation 1 below where: complex amplitude of signal light is $E_{sig}$; complex amplitude of reference light is $E_{ref}$. $\theta_{sig}$ and $\theta_{ref}$ are phases of the signal light and the reference light respectively according to the optical path length.

[Equation 1]

$$S = |E_{sig}|^2 |E_{ref}|^2 \cos(\theta_{sig} - \theta_{ref}) \quad (1)$$

Then the behavior of the boundary reflection light will be quantified. It is assumed that: wavelength of the optical source is λ; numerical aperture of the objective lens is NA; boundary position between the culture vessel and the specimen is z=0; deviation from the focus position of the objective lens is z. A detection signal S(z) is described with Equation 2 below in a case where phase diversity detection is performed while taking into account the defocus wavefront aberration included in the signal light.

[Equation 2]

$$S(z) = |E_{sig}|^2 |E_{ref}|^2 \text{sinc}^2\left(\pi \cdot \frac{z}{\lambda} NA^2\right) \quad (2)$$

Figure 2:
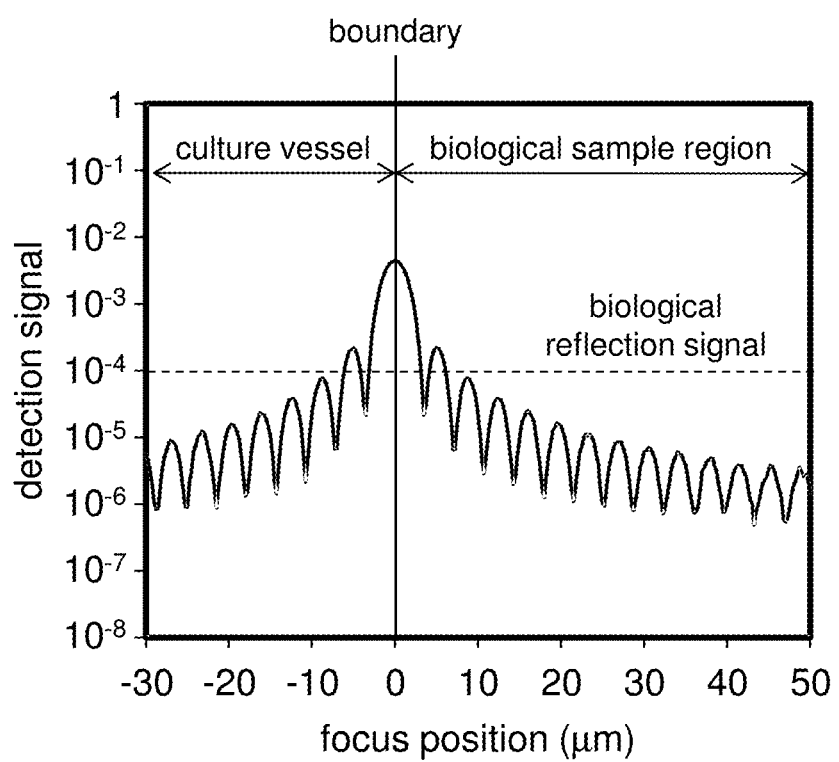
FIG. 2 illustrates a result where an influence of boundary reflection is calculated.

FIG. 2 illustrates a result where an influence of the boundary reflection is calculated. It is assumed that the wavelength of the optical source λ=780 nm and the numerical aperture of the objective lens NA=0.52 in Equation 1. The detection signal S is calculated acquired by a condition without the specimen (the vessel is filled with the culture solution only) using each of the refractive indexes above. The horizontal axis of FIG. 2 represents the focus position z of the objective lens. As can be seen in FIG. 2, the influence of the boundary reflection light is not limited to the boundary but is extended to observed areas including cells in accordance with sinc function. It is understood that a large crosstalk is caused with respect to the reflected signal from the cell. Hereinafter, as long as not specifically noted, it is assumed that the wavelength of the optical source is 780 nm and the numerical aperture of the objective lens is 0.52.

Patent Document 1 discloses a technique that changes phases based on optical path lengths of signal light and reference light. However, in the document, a detection signal is acquired depending on light intensity of reflected light from the specimen. Thus it may be difficult to reduce influences of the boundary reflection light as illustrated in FIG. 2.

Figure 3:
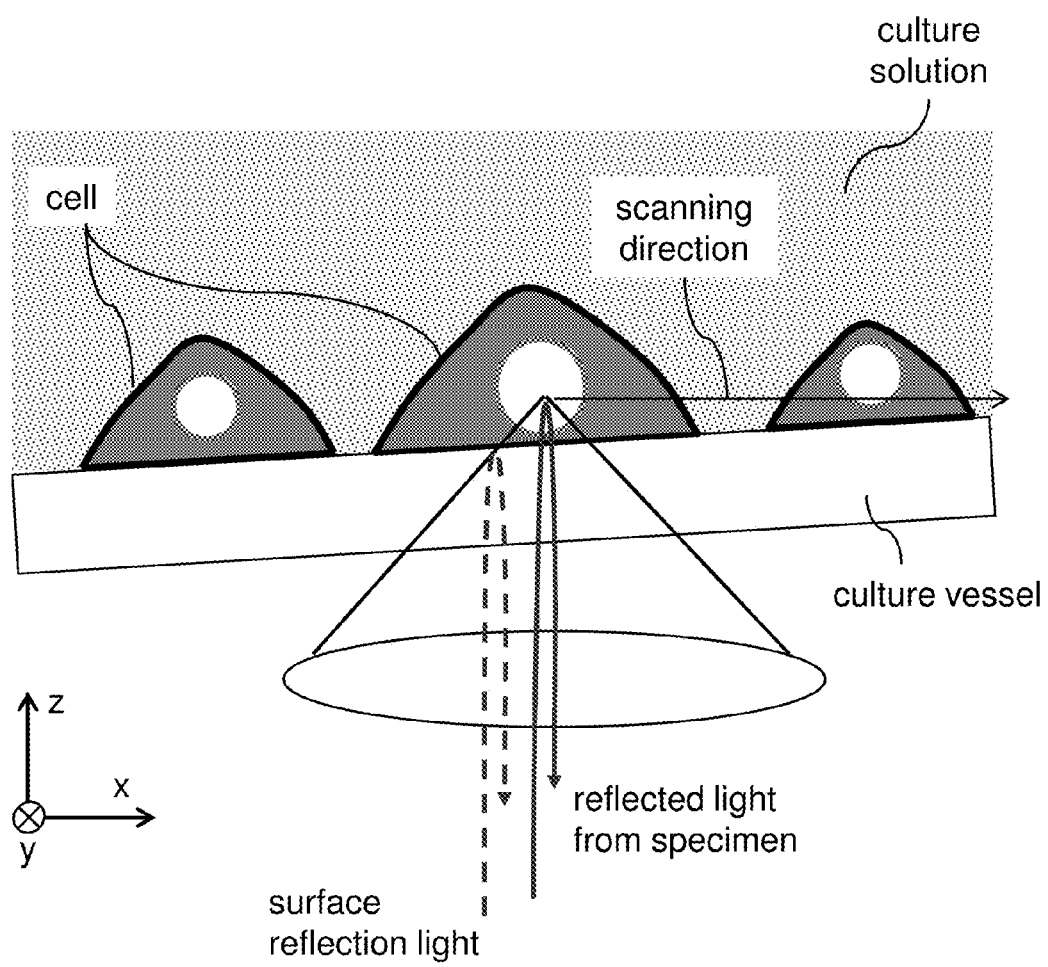
FIG. 3 is a schematic diagram in a case where the vessel is not perpendicular to an optical axis.

FIG. 3 is a schematic diagram in a case where the vessel is not perpendicular to an optical axis. In general, the culture vessel is not always perpendicular to the optical axis. Such cases occur depending on, for example, the mechanical precision of a vessel holder (not shown in the figure) or on the precision of forming the culture vessel when using plastic culture vessel.

When acquiring signals while scanning the objective lens or scanning the culture vessel along the scanning direction in FIG. 3, the distance in the z direction between the boundary of the culture vessel and the specimen varies depending on the position in the x direction. Therefore, the significance of influence of the boundary reflection light varies depending on the scanning position in the x direction. This example describes one dimensional scan. However, more generally speaking, the light is scanned two dimensionally in xy directions to acquire two dimensional images as measurement results. The objective of the embodiment 1 is, assuming general cases where the culture vessel is not perpendicular to the optical axis, to decrease the influence of the boundary reflection light, thereby measuring the number and size of the cells with high precision.

The embodiment 1 describes, for the sake of simplicity, a case where the detection signal is acquired using so-called phase diversity detection described in Patent Document 1. The OCT apparatus multiplexes the signal light with the reference light, and then uses an optical system that focuses the light onto an optical detector by detection lens. Assuming that the optical axis is set in the z axis, the aperture of the detection lens is formed in the xy plane. Assuming that: the z coordinate of the focus point of the objective lens is z; the z coordinate of the detection lens is $z_0$; and the interference between the signal light and the reference light is mathematized by superimposing the interferences at each point (x, y, $z_0$) on the aperture of the detection lens, the detection signal S is described by Equation 3 below.

[Equation 3]

$$S = \left| \iint_A E_{sig}(x, y, z_0) \cdot E_{ref}(x, y, z_0) dx dy \right|^2 \quad (3)$$

Equation 3 is generalized to address spatial distribution of signal light and spatial distribution of reference light at the aperture of the detection lens. Patent Document 1 assumes that the reference light is planar wave, thereby considering the phase only based on the optical path length. Thus Patent Document 1 uses reference light $E_{ref}$ described in Equation 4 below, assuming that the amplitude A and the optical path length L are constant values. $(2\pi/\lambda)L$ is a phase based on the optical path length of the reference light.

[Equation 4]

$$E_{ref}(x, y, z_0) = A \exp\left(i \frac{2\pi}{\lambda} L\right) \quad (4)$$

The signal light $E_{sig}$ is described in Equation 5 below as a sum of the boundary reflection light and the reflected light from a plurality of cells. The first term of the right side describes the planar boundary reflection light considering defocus wavefront aberration. $E_b$ is an amplitude reflection index. R is an aperture radius of the detection lens. The second term of the right side describes a sum of reflection light from each tissue in the biological body. The second term represents waves having wavenumber components more than the boundary reflection light, because each tissue has three dimensional shapes.

[Equation 5]

$$E_{sig}(x, y, z_0) = E_b \exp\left\{i \frac{2\pi}{\lambda}\left(\frac{x^2+y^2}{R^2} NA^2 z + L\right)\right\} + \sum_n E_n(x, y, z_0) \quad (5)$$

In Equations 4 and 5, when using phase diversity detection, it can be assumed that L=0. Now zero is assigned to the second term of the right side, Equations 4 and 5 are assigned to Equation 3, and $E_b$ is rewritten to $E_{sig}$. Then the result matches with Equation 2.

In order to quantify the influence of the boundary reflection, a method is required to solve Equation 3 numerically. In this example, Monte Carlo method is applied and ray tracing is basically used, and the interference calculation is rendered available by extracting wavefront information from ray trajectories, thereby developing a simulation method addressing phase diversity detection. Briefly speaking, phase information depending on optical path length and intensity information depending on amplitude are calculated in addition to positional information and velocity information as information associated with each optical ray, thereby solving Equation 3 numerically at the aperture of the detection lens. This method calculates: (a) changes in optical ray vector due to refraction at the surface of the object; and (b) amplitude reflection index and transmission factor depending on incident angle and polarization according to Fresnel equations. Hereinafter, this method is referred to as wave-like ray tracing method.

In order to verify calculation accuracy of wave-like ray tracing method, an OCT apparatus using an optical system as in FIG. 4 of Patent Document 1 (wavelength 780 nm, numerical aperture of objective lens 0.52), and a sample using polystyrene quasi blood cell (refractive index is about 1.59) available on the market as measurement sample, are prepared. The quasi blood cell has a size approximately as large as the cells mentioned above, although the refractive index is different.

FIG. 4 compares a simulation result for xy images with a measurement result by OCT device. A sample is used in which water and quasi blood cells are dispersed in single layer between a glass substrate and a cover glass. A simulation is performed assuming that: the quasi blood cell is a spherical object with diameter of 10 µm; 13 quasi blood cells are regularly placed.

FIG. 4(a) illustrates a result in which the detection signal intensity is calculated while changing the focus position of the objective lens in an area of 100×100 µm divided into mesh points with intervals of 0.5 µm. One million optical rays are used to calculate each mesh point. FIG. 4(b) illustrates an example of measurement result. According to FIG. 4(a) and FIG. 4(b), it is understood that the calculation result and the measurement result are approximately identical to each other in characteristics. Thus wave-like ray tracing method is capable of calculating image data acquired by OCT. In addition, as seen in FIG. 4(b), the measurement result includes a portion where the average brightness of the image is high and a portion where the average brightness of the image is low, in the y direction. This is due to the influence of the vessel surface inclined to the optical axis, as mentioned above.

FIG. 5 is a calculation model in a case where cells are adhered to the boundary of the culture vessel. This example illustrates a case where the boundary of the culture vessel is not perpendicular to the optical axis (z axis). In this model, now it is assumed that the focus position is scanned in the x direction as shown in FIG. 5.

Figure 6:
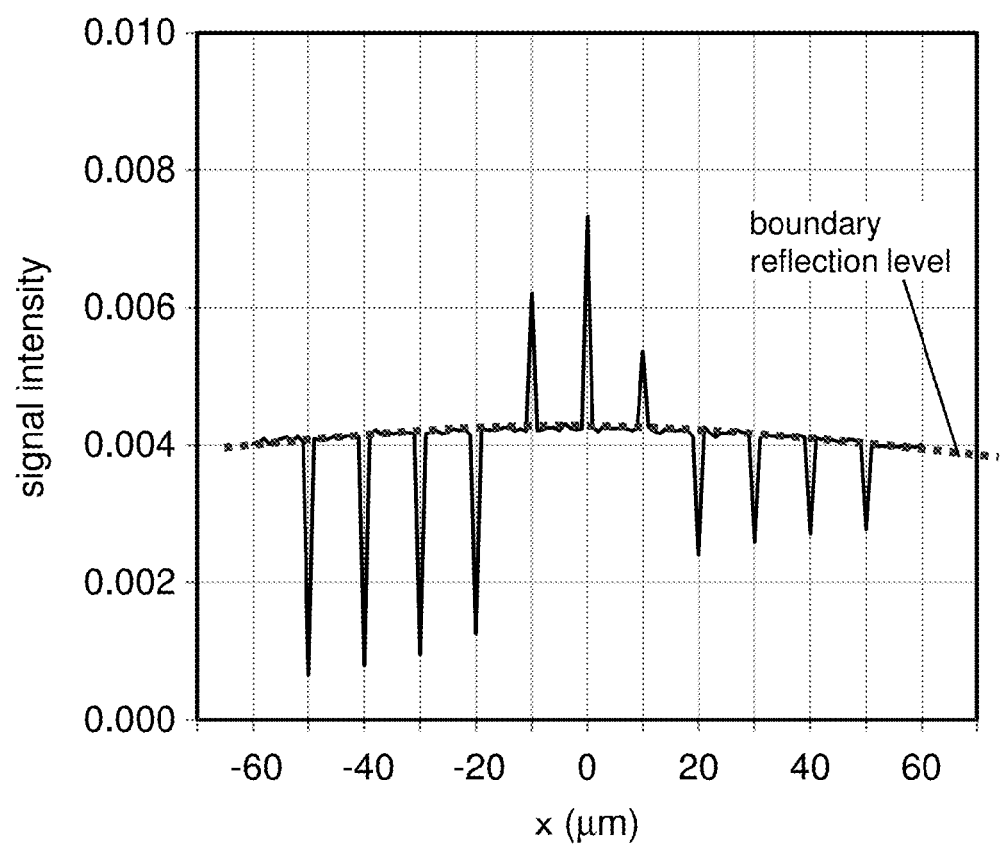
FIG. 6 is an example of simulation result.

FIG. 6 is an example of simulation result. In this example: the inclination of the culture vessel is at a ratio of 1/100 with respect to xz; the cells as observed targets have diameter of 1 µm and are placed at interval of 10 µm in the x direction. The z position of the focus point is assumed constant at the boundary between the culture vessel and the cell at the center of the scanned area (x=0). Other conditions are same as above. The signal intensity in vertical axis corresponds to reflection index.

As seen in FIG. 6, the signal intensity has 11 peaks corresponding to cell positions, and the peaks include fluctuations both in plus side and minus side with respect to the boundary reflection level described by dotted line. This is because of influence in which the boundary reflection and the reflected light at both lower and upper surfaces of the cell are interfered with each other in terms of wave behavior. This is caused by the significant effect of the interference because the cell size is smaller than that of the quasi blood cell (diameter 10 µm) shown in FIG. 4. It is difficult to detect cells by digitizing the measurement signal using a prefixed threshold for such measurement signals or such images.

<Embodiment 1: Measurement Procedure>

Figure 7:
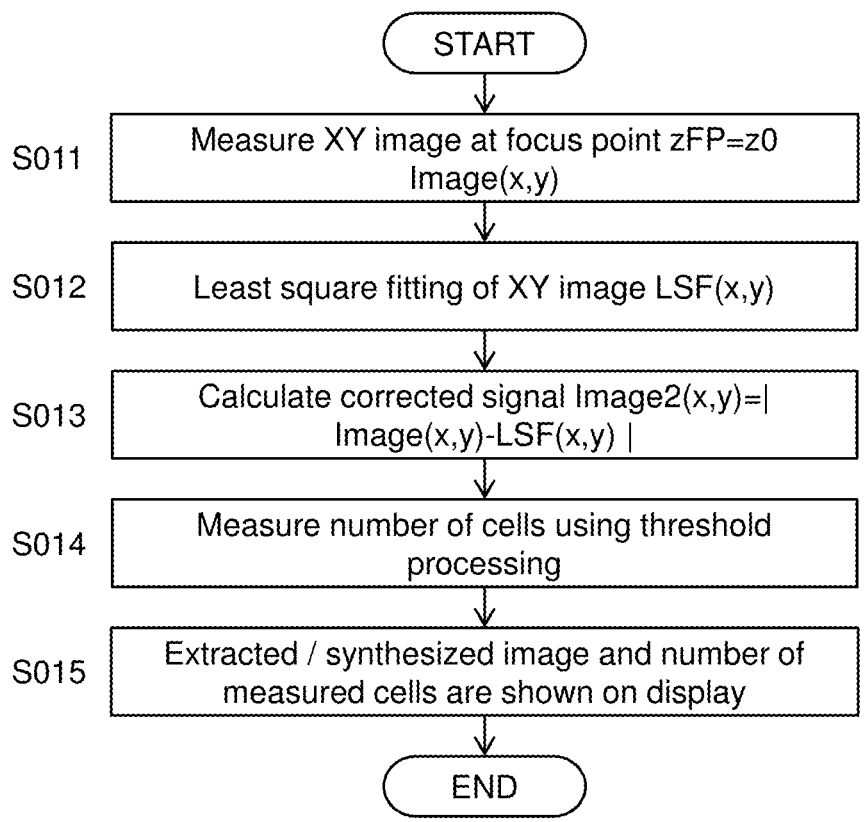
FIG. 7 is a flowchart describing an optical measurement method according to an embodiment 1.

FIG. 7 is a flowchart describing an optical measurement method according to the embodiment 1. Hereinafter, each step in FIG. 7 will be described.

(FIG. 7: Step S011)

The objective lens of the OCT apparatus is set so that the focus point zFP=z0. Two dimensional data Image(x, y), which is an observation image in xy plane, is acquired using signal intensities acquired by scanning the detection light in xy directions.

(FIG. 7: Step S012)

A boundary reflection signal level LSF(x, y) is calculated by performing least square fitting to Image(x, y) using quadratic function, for example. LSF(x, y) corresponds to a function in which the boundary reflection level in FIG. 6 is approximated.

(FIG. 7: Step S013)

A corrected signal intensity Image2(x, y) is calculated using Equation 6 below. By using the corrected signal intensity Image2(x, y), it is possible to remove influences of boundary reflection from the detection signal, thereby acquiring signals having peaks with plus value reflected from the cell.

[Equation 6]

$$\text{Image2}(x,y) = |\text{Image}(x, y) - LSF(x, y)| \qquad (6)$$

(FIG. 7: Step S014)

The cell is identified using appropriate threshold to count the number of the cells. For example, it is possible to measure the number of the cells by assuming that the cell exists at portions having signal values more than the threshold, and by counting the number of such points.

(FIG. 7: Step S015)

One or more of following are selected: (a) Image(x, y), (b) Image2(x, y), (c) number of cells measured. It is shown on a display, for example.

Figure 8:
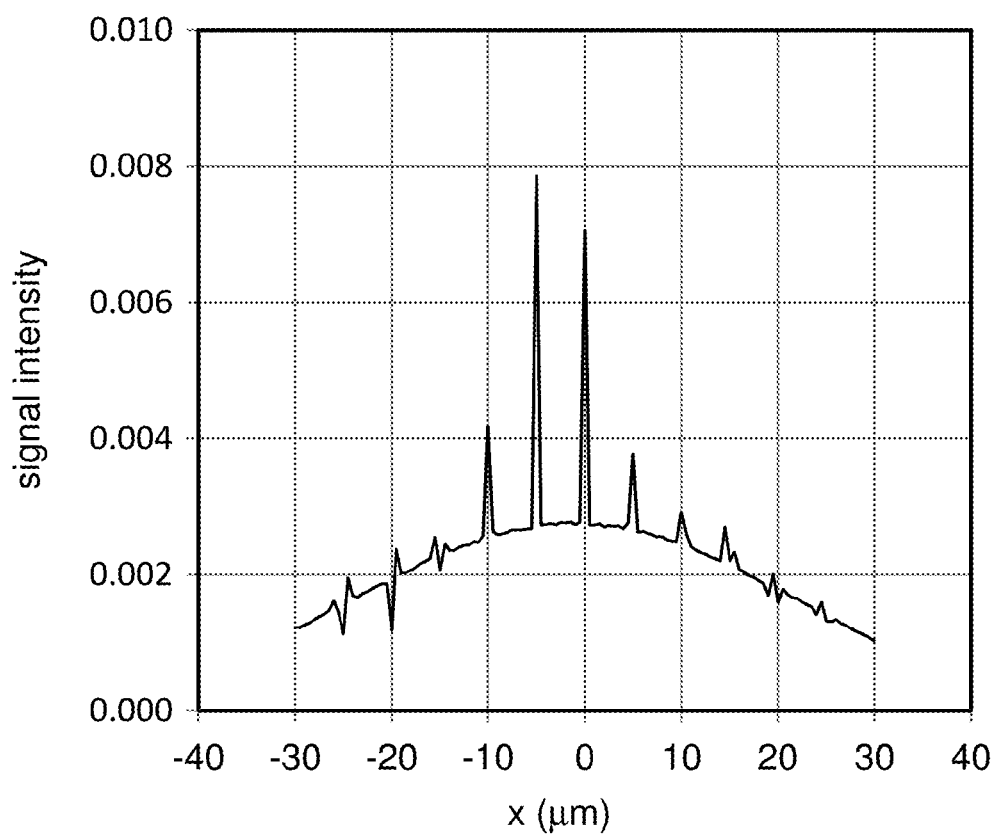
FIG. 8 is another example of simulation result apart from FIG. 6.

FIG. 8 is another example of simulation result apart from FIG. 6. This example assumes that the inclination of the vessel boundary is ten times of FIG. 6 (ratio of 10/100 with respect to xz). It is further assumed that: diameter of the cell is 1 µm; cycle is 5 µm; calculation interval is 0.5 µm; the z position of the focus point is set at the vessel boundary at x=0 as in FIG. 5. Since the vessel inclination is larger than that of FIG. 6, it is understood that changes in signal intensity of vessel boundary with respect to x value and changes in cell signals are large.

FIGS. 9(a) and 9(b) are examples of xy images respectively illustrating a simulation result of detection signal and a result where the measurement method according to the embodiment 1 is performed. This example shows a result where the z position of the focus point is shifted upward by 2 µm from the vessel boundary at x=0.

FIG. 9(a) is a simulation result of the detection signal. Because of influence of the vessel boundary inclination, the detection signal is inverted at right edge (plus side in x direction) and the detection signal is small at left edge (minus side in x direction) causing low contrast.

FIG. 9(b) is the corrected signal intensity Image2(x, y) calculated in accordance with the procedure of FIG. 7. The cell contrast is improved at regions from the center to right side. It shows that the quality of data is improved so that detection may be more easily performed. The left edge may not be well detected. However, it is due to influence of the large inclination of substrate boundary of 10/100. If the inclination is small, the cell peaks are clear as in FIG. 6, and thus the method is capable of measuring the number of cells with high precision.

<Embodiment 1: Summary>

With the optical measurement method according to the embodiment 1, it is possible to measure the number and size of cells with high precision by reducing the influence of signals reflected from the vessel boundary.

<Embodiment 2>

Figure 10:
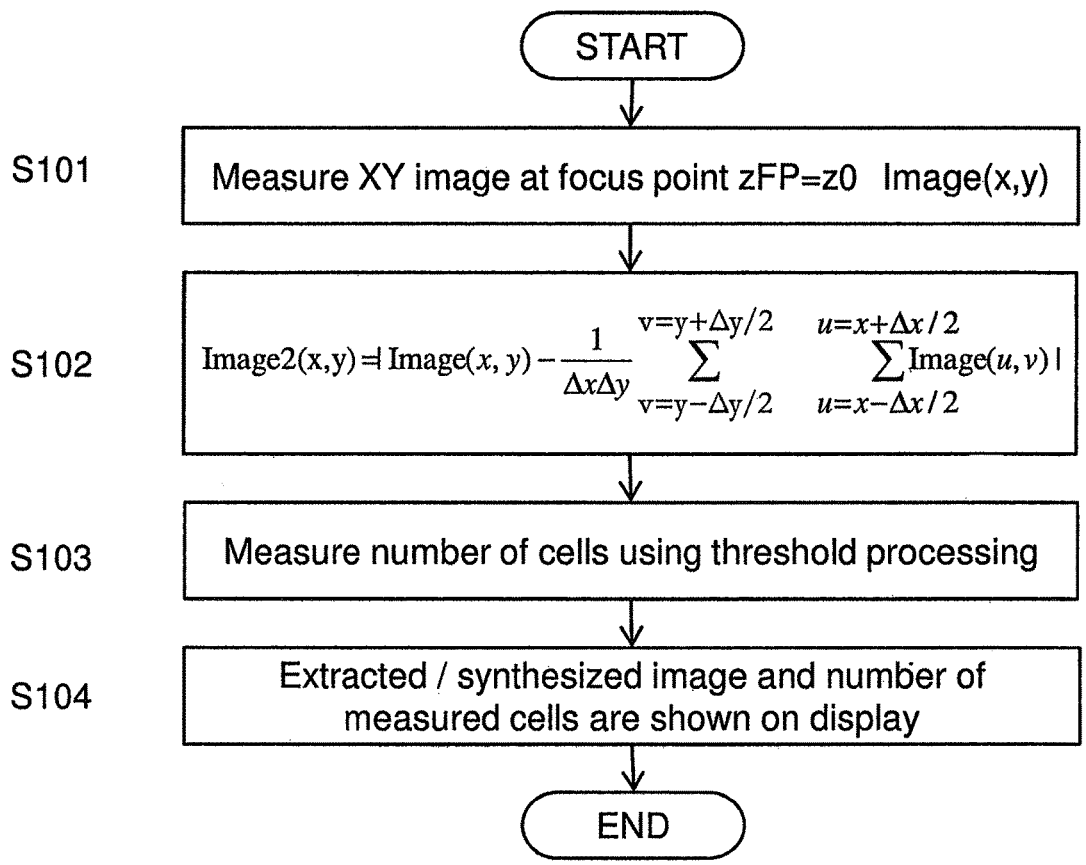
FIG. 10 is a flowchart describing an optical measurement method according to an embodiment 2.

FIG. 10 is a flowchart describing an optical measurement method according to an embodiment 2 of the present invention. Hereinafter, each step in FIG. 10 will be described.

(FIG. 10: Step S101)

The objective lens of the OCT apparatus is set so that the focus point zFP=z0. Two dimensional data Image(x, y), which is an observation image in xy plane, is acquired using signal intensities acquired by scanning the detection light in xy directions.

(FIG. 10: Step S102)

A corrected signal intensity Image2(x, y) is calculated using Equation 7 below. Equation 7 subtracts an average value of the detection signal in a peripheral area (Δx, Δy) around a point (x, y) from Image2, and then acquires an absolute value thereof. Equation 7 subtracts only the average value of the detection signal in the peripheral area, which is different from the embodiment 1. Thus it is possible to remove the influence of the boundary reflection with calculation load smaller than that of the embodiment 1. The corrected signal intensity Image2(x, y) is a signal having peaks with plus values reflected from the cell, as in the embodiment 1. Preferably, the values of Δx and Δy are approximately larger than the size of the cell as observation target and are approximately smaller than the average distance between cells determined by the density of the specimen.

[Equation 7]

$$\text{Image2}(x, y) = \left| \text{Image}(x, y) - \frac{1}{\Delta x \Delta y} \sum_{v=y-\Delta y/2}^{v=y+\Delta y/2} \sum_{u=x-\Delta x/2}^{u=x+\Delta x/2} \text{Image}(u, v) \right| \quad (7)$$

(FIG. 10: Steps S103 to S104)

These steps are same as steps S014 to S015 in the embodiment 1.

FIGS. 11(a) and 11(b) are examples of xy images respectively illustrating a simulation result of detection signal and a result where the measurement method according to the embodiment 2 is performed. The calculation conditions is same as in FIG. 9. Δx=Δy=4 μm.

FIG. 11(a) is a simulation result of the detection signal. FIG. 11(b) is the corrected signal intensity Image2(x, y) calculated in accordance with the procedure of FIG. 10. The contrast at the left edge (minus side in x direction) is significantly improved compared to FIG. 9(b).

On the other hand, bright regions with ring-like shape are observed around signal peaks representing the cell position. This is inevitable because the average of detection signal of the peripheral area is subtracted. However, the distance from the peak to the ring is mathematically determined according to (Δx, Δy). Thus it is easy to identify the cell position with threshold processing using such as pattern matching. In addition, the bright point at the center of the cell position and the peripheral ring are both caused by the detection signal from the cell. Thus the ring can be removed by deconvolution, for example. Such processing may be easily performed using general image processing tool such as OpenCV.

<Embodiment 2: Summary>

The optical measurement method according to the embodiment 2 does not perform boundary fitting using such as least square method. Thus it is possible to suppress calculation load compared to the embodiment 1. In addition, it is beneficial that the detection signal with low contrast is significantly improved.

<Embodiment 3>

An embodiment 3 of the present invention describes a method for measuring specimens by acquiring a plurality of detection results each having different focus points in the optical axis direction of the detection light, and by combining the detection results.

FIG. 12 is another calculation model in a case where cells are adhered to the boundary of the culture vessel. As in the embodiments 1 and 2, the coordinate system is configured so that the boundary position of the culture vessel at x=0 is set as z=0. The z axis is parallel to the optical axis. In this model, as shown with dotted lines in FIG. 12, two or more of focus points are prepared in the z direction. The detection signal is acquired by scanning the detection light in the x direction for each of the focus points.

Figure 13:
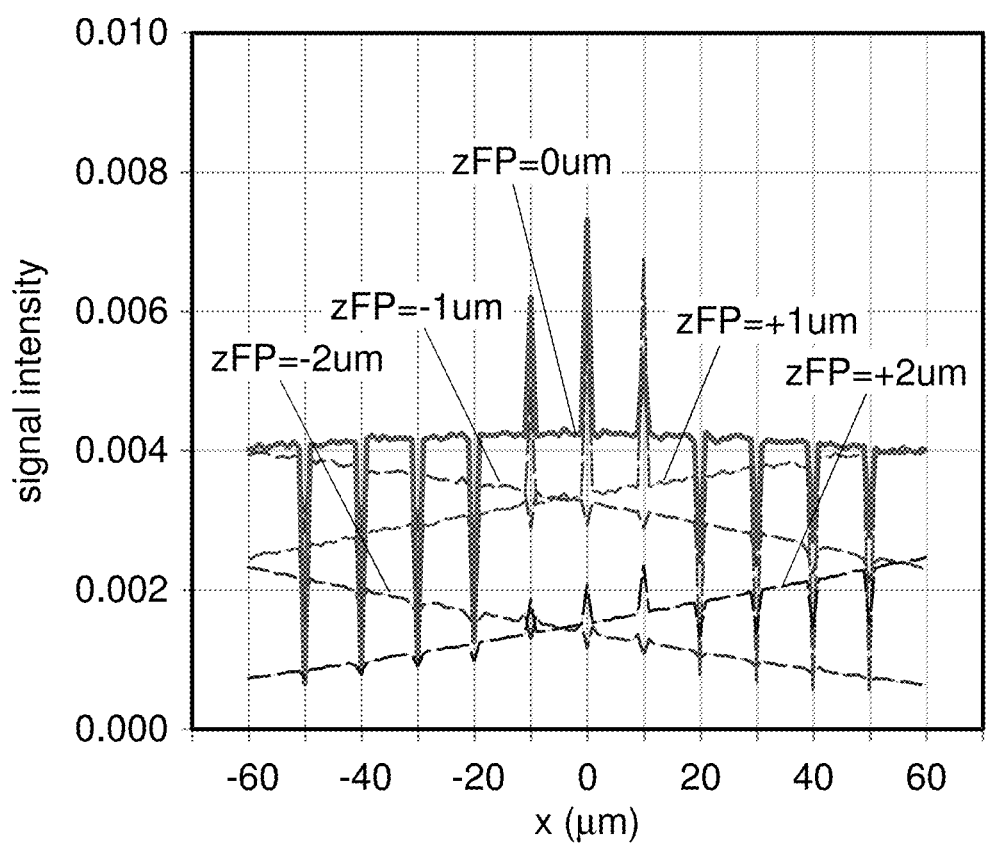
FIG. 13 is an example of simulation result of detection signal.

FIG. 13 is an example of simulation result of detection signal. This example illustrates a relationship between x and the detection signal under five conditions of: focus position of the objective lens zFP=−2 μm, −1 μm, 0 μm, +1 μm, and +2 μm. The inclination of the substrate boundary is same as in FIG. 6 (ratio of 1/100 with respect to xz). The diameter of the cell is 1 μm. The cycle is 10 μm. The calculation interval is 0.5 μm.

Now the discussion is directed to the boundary reflection signal level. In a case of zFP=0 μm, the signal level has a symmetrical characteristic with respect to the x axis. In a case where zFP is positive, the signal characteristic monotonically increases positively. In a case where zFP is negative, the signal characteristic monotonically decreases negatively. The pair of zFP=±1 μm and the pair of zFP=±2 μm are asymmetrical to each other with respect to the x axis, respectively. This is because the selectivity in z direction of Sinc function in Equation 2 and FIG. 2 is an even function with respect to the z axis. As in the embodiments 1 and 2, the peaks corresponding to the reflected light from the cell have positive and negative peaks due to influence of interference with the reflected light at the boundary.

By using measurement results with two or more of zFPs (e.g. the pair of zFP=±1 μm), it is possible to identify that the detection light changes from negative slope characteristic to positive slope characteristic along with increase in zFP, thereby identifying that the boundary of the culture vessel has an inclination of positive slope. In addition, by using increase ratio/decrease ratio of the detection signal in x direction and Sinc function in Equation 2, it is possible to measure the amount of inclination of the vessel boundary. It is noted that the amplitude of positive and negative peaks corresponding to reflected light from the cell have a characteristic that decreases when absolute value of zFP increases (i.e. the focus point is shifted from the specimen), as in the amplitude of the detection signal corresponding to the reflected light from the vessel boundary. This will be described in step S143 later.

Figure 14:
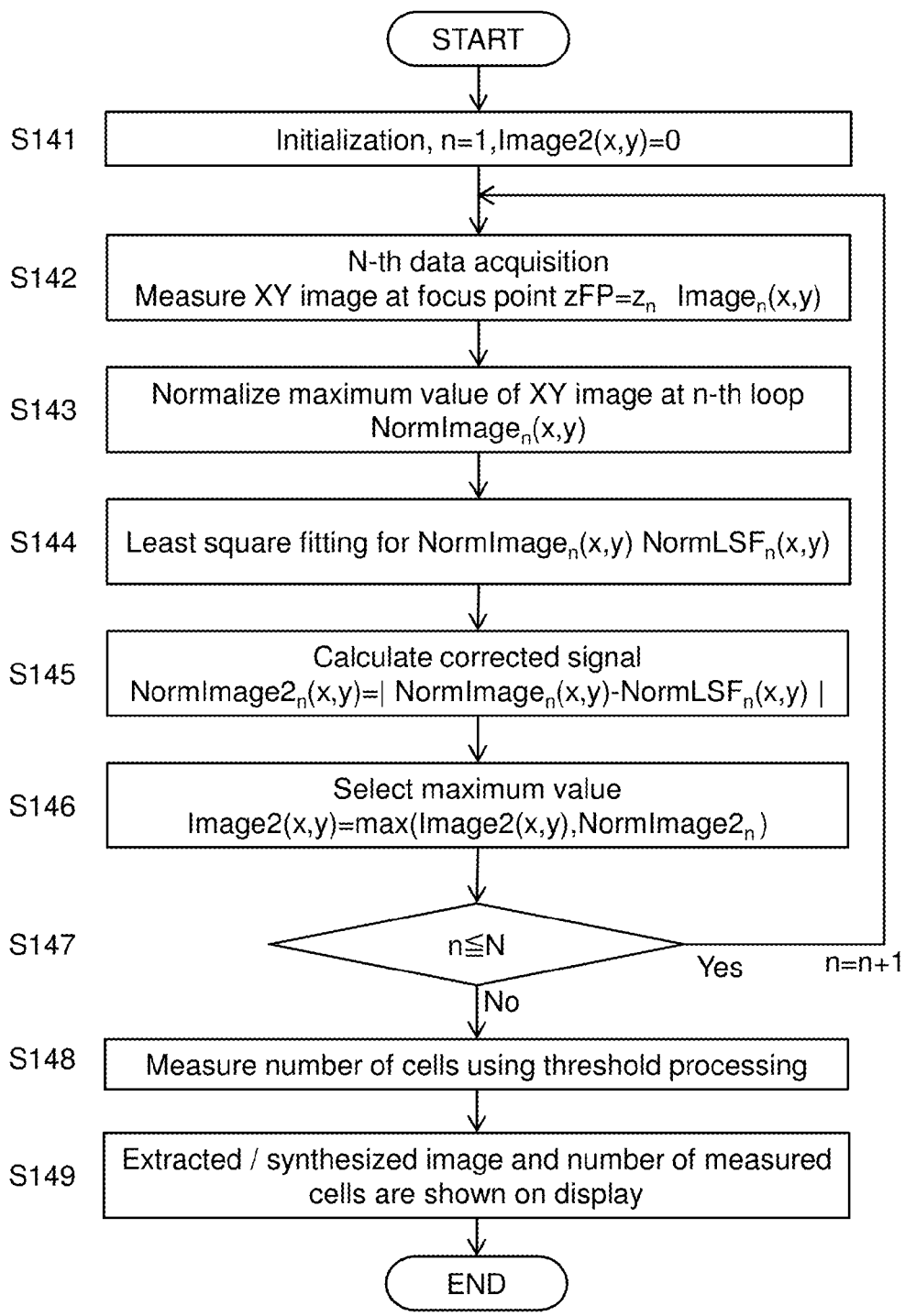
FIG. 14 is a flowchart describing an optical measurement method according to an embodiment 3.

FIG. 14 is a flowchart describing an optical measurement method according to the embodiment 3. Hereinafter, each step in FIG. 14 will be described.

(FIG. 14: Step S141)

The OCT apparatus and the measurement condition are initialized. The corrected signal intensity Image2(x, y) is zeroed. Parameter n is initialized as n=1. n is a loop counter. Different focus points (z direction) are set for each loop to acquire xy images.

(FIG. 14: Step S142)

The focus point of the objective lens of the OCT apparatus is set at a designated value for n-th loop (zFP=zn). Two dimensional data of signal intensity Imagen(x, y) is acquired by xy scan.

(FIG. 14: Step S143)

The embodiment 3 combines a plurality of detection signals each having different focus points. However, as shown in FIG. 13, the signal peak decreases as the focus point shifts from the specimen toward the z direction. Thus in this step, NormImagen(x, y) in which the measurement data is normalized is calculated in order to align the signal peaks for each focus point. Normalization may be performed by such as: (a) a method of aligning the maximum value of detection signal intensity at a predetermined value; (b) a method of aligning the average value of detection signal intensity at a predetermined value. FIG. 14 uses the method with maximum value.

(FIG. 14: Step S144 to S145)

The detection signal NormLSFn(x, y) reflected from the vessel boundary is calculated using such as least square fitting (S144). A corrected signal intensity NormImage2$n$(x, y) is calculated using Equation 6 (S145).

(FIG. 14: Step S146)

The detection signal may be maximum when the focus position in the z direction matches with the cell position. Then this step preserves the maximum value among detection signals for each focus point. Specifically, Image2(x, y) is compared with NormImage2$n$(x, y), and the value of larger one is set as Image2(x, y).

(FIG. 14: Step S147 to S149)

If the loop counter has not reached the maximum value N, the process returns to step S142 (S147). If reached, processes as in steps S014 to S015 in the embodiment 1 are performed (S148 to S149).

FIGS. 15(*a*) and 15(*b*) are examples of xy images respectively illustrating a simulation result of detection signal and a result where the measurement method according to the embodiment 3 is performed. The calculation condition is same as in FIGS. 9 and 11. The inclination of the vessel boundary is at ratio of 10/100 with respect to xz. The diameter of cell is 1 μm. The cycle is 5 μm. The calculation interval is 0.5 μm. Five z positions of the focus point are prepared (zFP=−2 μm, −1 μm, 0 μm, +1 μm, and +2 μm). The number of measurement N=5. The measurement data is normalized so that the maximum intensity is set as brightness of 255.

FIG. 15(*a*) is a simulation result of the detection signal. FIG. 15(*b*) is the corrected signal intensity Image2(x, y) calculated in accordance with the procedure of FIG. 14. It is understood that signals with clear contrasts are acquired across overall measured regions. Compared to FIG. 9(*b*) and FIG. 11(*b*), this method is capable of measuring the number of cells with the highest precision.

<Embodiment 3: Summary>

The optical measurement method according to the embodiment 3 acquires two or more of detection signal data sets each having different focus positions of the objective lens, thereby detecting the amount of inclination of the vessel boundary and the orientation of the inclination. Since the amount of inclination of the vessel boundary is constant, it is possible to improve the accuracy of least square fitting for xy image such as shown in FIG. 1, by combining the measurement results with two or more of the focus points.

<Embodiment 4>

An embodiment 4 of the present invention describes a method that acquires a plurality of detection results each having different focus points in the optical axis direction of the detection light as in the embodiment 3, and that measures the size of specimen using those detection results.

FIG. 16(*a*) is a schematic diagram illustrating a calculation model in a case where a plurality of cells with different sizes is placed at positions sufficiently away from the boundary of the culture vessel. This example uses a coordinate system with the center position of the cell as z=0. In this model, as shown with dotted lines in the figure, two or more of focus points in the z axis direction are prepared. The detection signal is acquired by scanning the detection light in the x direction at each focus point.

FIG. 16(*b*) illustrates a schematic diagram of signals measured with the OCT apparatus of the present invention. If the cell size is smaller than the light spot size which is determined by wavelength/objective lens numerical aperture of the optical source, the acquired signal has a maximum value depending on the cell size and its characteristic has Gaussian distribution which half width is approximately same as the spot size. Therefore, the size of specimen which is as large as or is smaller than the optical spot size may be quantified by the maximum value of the acquired signal. This embodiment previously stores the maximum value of the signal depending on the cell size in a database or in a data table. The optical spot is scanned in xyz directions to determine the maximum signal value acquired when the center of the optical spot approximately matches with the center of the cell. The maximum value is compared with the database to measure the cell size which is as large as or is smaller than the optical spot.

Figure 17:
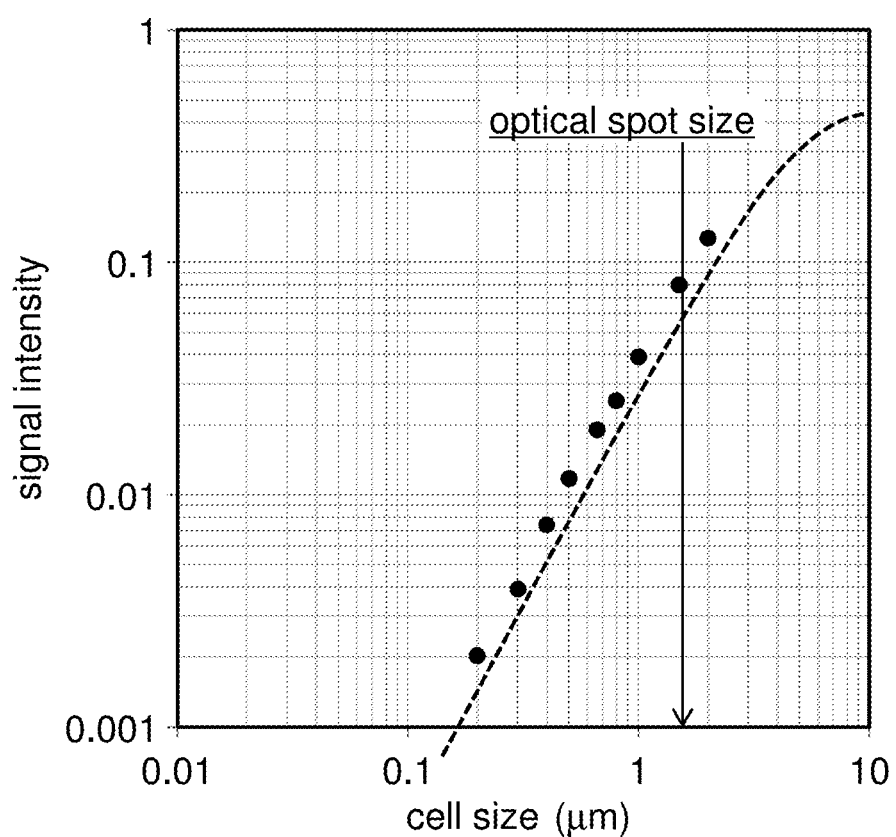
FIG. 17 is a simulation result illustrating a relationship between a diameter of a cell and a signal intensity.

FIG. 17 is a simulation result illustrating a relationship between the diameter of the cell and the signal intensity. Interference of reflected light occurs at the incident side and at the back side depending on the cell size. In order to describe only the dependency on cell size, the result illustrates a case where the light is reflected at the incident side (hemisphere surface at the side closer to the lens) only. The focus point of the lens is z=0. It is understood from the calculation result that the signal intensity increases depending on the cell size (=diameter). As shown in the figure, such characteristic may be utilized assuming that the characteristic is consecutive until the cell size reaches two to three times larger than the optical spot size.

Assuming that the wavelength λ of the optical source is 0.78 μm and the numerical aperture NA of the objective lens is 0.52, the optical spot size at the focus point surface is λ/NA=1.5 μm. If the observed cell size is larger than the optical spot size (i.e. approximately larger than 1.5 μm), the cell size is measured using such as half width of detection signal intensity. If the observed cell size is smaller than the optical spot size (i.e. approximately smaller than 1.5 μm), the detection signal intensity acquired by scanning the light in x direction forms Gaussian distribution, and the cell size cannot be measured by half width or the like. On the other hand, the maximum value of detection signal intensity is determined by the cell size as shown in FIG. 17. Thus this method is beneficial in that the cell size may be measured without depending on half width.

Figure 18:
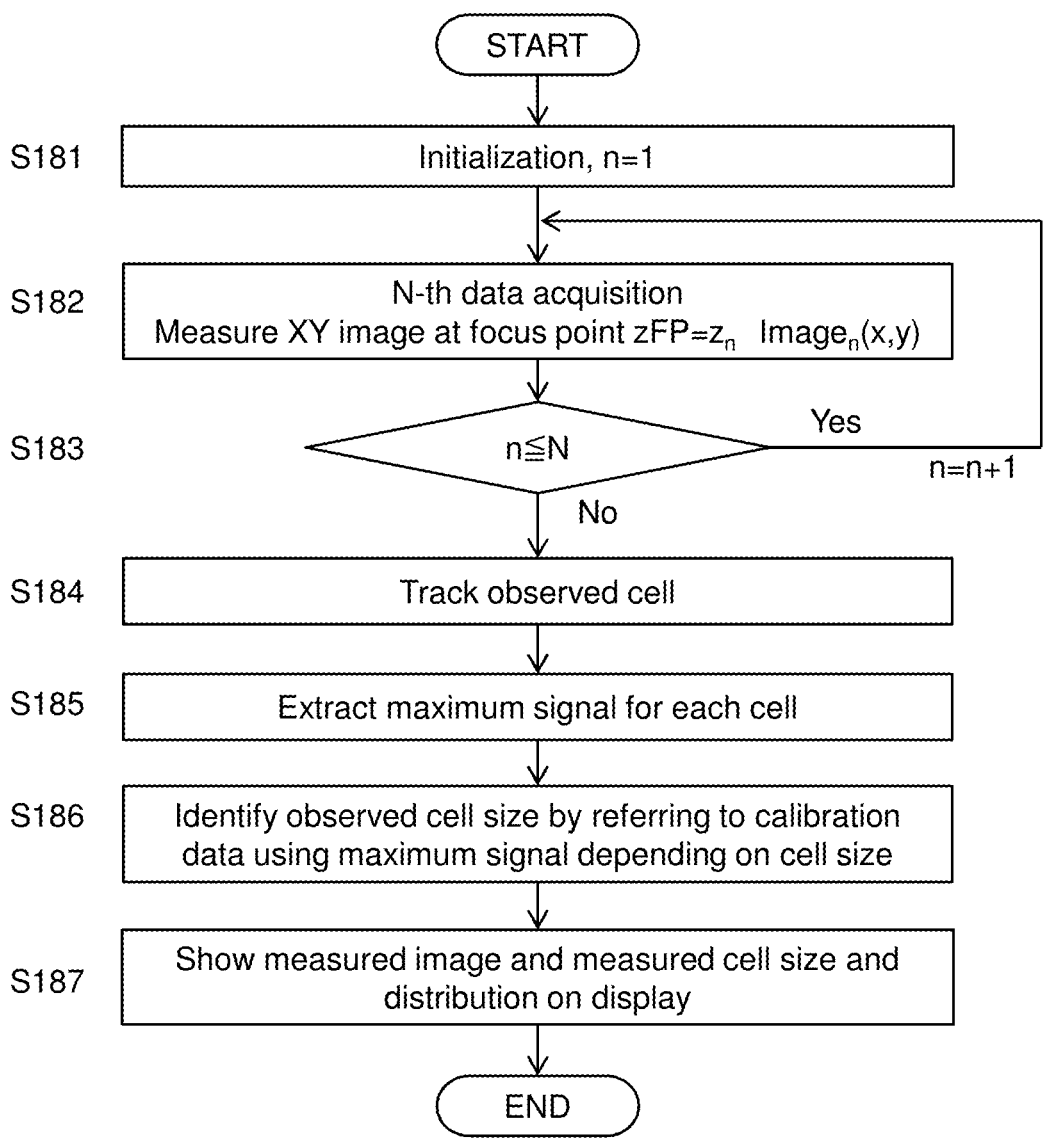
FIG. 18 is a flowchart describing an optical measurement method according to an embodiment 4.

FIG. 18 is a flowchart describing an optical measurement method according to the embodiment 4. This flowchart assumes that the relationship between the signal intensity and the cell size described in FIG. 17 is acquired as calibration data in advance. Hereinafter, each step in FIG. 18 will be described.

(FIG. 18: Steps S181 to S183)

Steps S181 to S182 are same as steps S141 to S142 in FIG. 14. If the loop counter has not reached the maximum value N, step S182 is repeated, otherwise the process proceeds to step S184 (S183).

(FIG. 18: Steps S184 to S185)

The observed cell does not always keep still and may always repeat small movements randomly by Brownian motion, for example. Then the specimen is tracked using so-called object identification algorithm (S184). The maximum value of the detection signal is extracted according to defocus and to changes in amplitude of detection signal, for each of cells (S185).

(FIG. 18: Steps S185: Additional Note)

The maximum value of the detection signal may be calculated by such as: (a) a method of calculating the mechanical maximum value; (b) a method of calculating the maximum value by performing maximum likelihood fitting in which positional fluctuation due to Brownian motion is integrated using polynomial approximation and least square method. The former method is excellent in simplicity but it is necessary to configure the focus movement step size in z direction sufficiently smaller than the focus depth determined by Equation 2 (approximately at size of wavelength). The latter method uses all observed data and thus the calculation is complexed. However, the latter method is excellent in that the focus movement step size in z direction may be larger than that of the former method.

(FIG. 18: Steps S186)

The cell size is identified by referring to the calibration table shown in FIG. 17 using the maximum value of detection signal. The maximum value of detection signal varies mainly depending on its refractive index. Thus the calibration table may be previously prepared according to the detection signal calculated from cell samples with known size. The calibration table may be prepared by calculating macroscopic refractive index based on conventional evaluation method such as specific gravity measurement, element analysis, or optical scatter characteristics, and by using another method such as the aforementioned method or using numerically calculated result according to calculation methods such as conventional FDTD (Finite Deferential Time Domain) method.

(FIG. 18: Steps S187)

The imaged detection signal, the measured cell size, and the size distribution may be arbitrarily selected and may be shown on a display.

Since the focus point of lens does not always match with the center position of the cell, it may be difficult to measure the size of cells using the relationship of FIG. 17 from the measurement results directly. Then hereinafter, another example of the embodiment 4 will be described in which the cell size is measured by combining measurement results at a plurality of focus positions as in the embodiment 3.

FIGS. 19(a) to 19(f) are simulation results illustrating a two dimensional observation image acquired by performing an xy scan to cells with different sizes while changing the focus position. In this example, the cell diameters are 0.1, 0.2, 0.3, 0.5, 0.7, 1.0, and 1.5 μm each assigned from the left side in the x direction. The cell size in the y direction is same for each cell. The intervals between cells are 5 μm in xy directions respectively. For the sake of readily understanding the spirits of the present invention, the detection signal intensity of each cell is normalized by the maximum signal intensity at z=0, reflecting the result in FIG. 19.

FIGS. 19(a) to 19(f) are simulation results at the focus positions of the lens zFP=0, −0.1, −0.2, −0.5, −1.0, and −1.5 μm, respectively. It is understood from those results that: when the cell size is small, the attenuation in detection signal intensity is large with respect to the defocus, and clear contrast data may be acquired only around the focus point; when the cell size is large, the attenuation in detection signal intensity is small with respect to the defocus, and the detection signal may be acquired from the cell even when the defocus is large. By utilizing this relationship, it is possible to determine the cell size by calculating the attenuation ratio of the detection signal with respect to the defocus from the measurement results at two or more of focus points.

FIGS. 20(a) to 20(c) are schematic diagrams illustrating a relationship between defocus and detection signal and cell size. FIG. 20(a) geometrically illustrates an optical system that includes a defocus with respect to small cells. The geometrical beam size at z position of the cell is geometrically determined by the numerical aperture of the objective lens and the amount of defocus. The detection signal attenuates depending on the ratio of projection area size of the cell in the geometrical beam area size. This ratio of projection size corresponds to reaction cross section. When the cell size is small, the reaction cross section is smaller than that of when the cell size is large as shown in FIG. 20(b). Therefore, the attenuation ratio of the detection signal differs depending on the cell size.

FIG. 20(c) is a schematic diagram illustrating a relationship between attenuation ratio of detection signal and cell size. The simulation using wave-like ray tracing is based on ray tracing. Thus it is not possible to precisely address Mie scattering or Rayleigh scattering. However, it is obvious that the reaction cross section is asymptotic to geometrical approximation when the defocus is large. It is possible to identify the cell size by previously preparing calibration data acquired by measuring the relationship of FIG. 20(c) from practical specimens, and by measuring the attenuation of detection signal with respect to the defocus.

Figure 21:
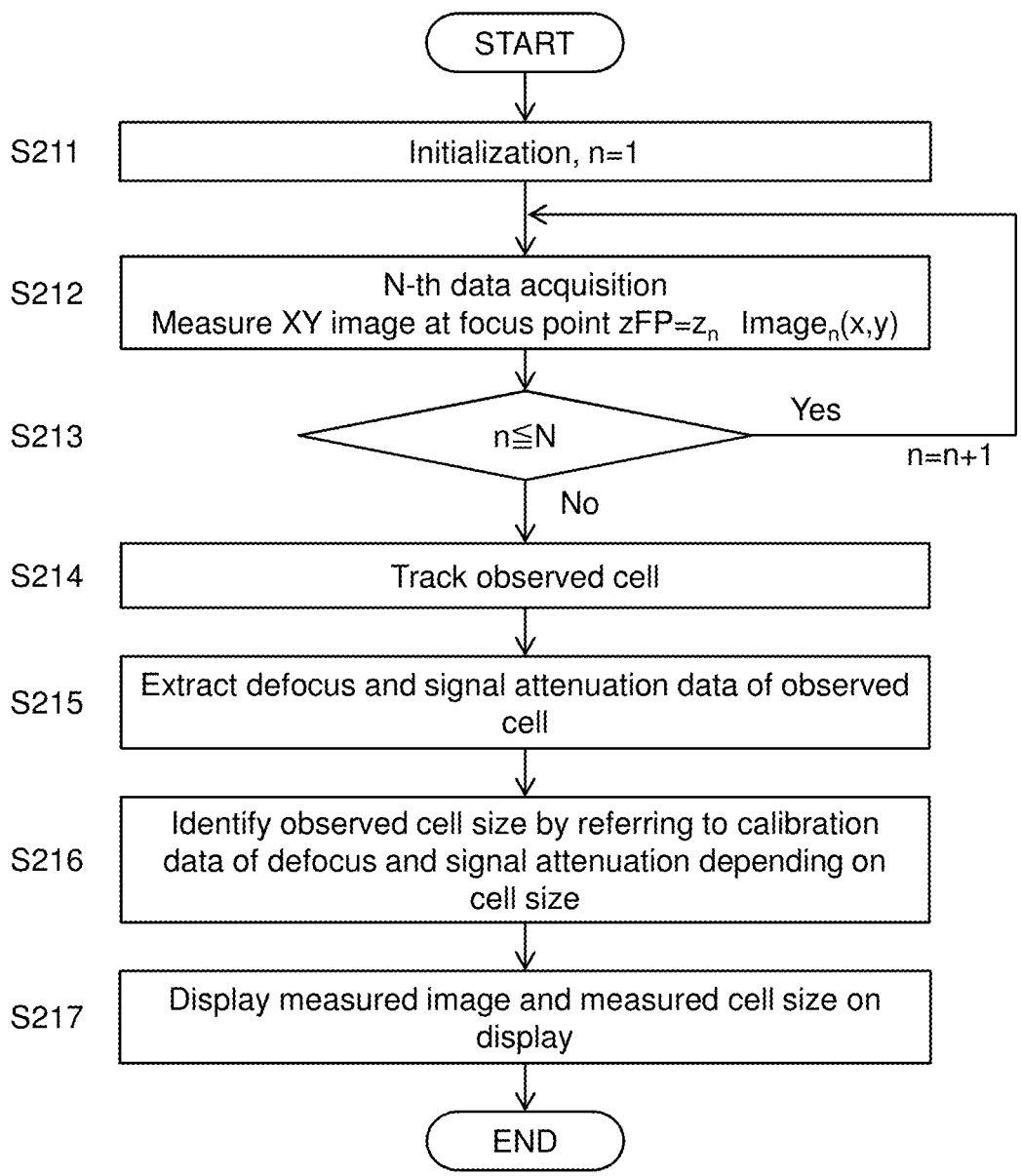
FIG. 21 is a flowchart illustrating another example of the optical measurement method according to the embodiment 4.

FIG. 21 is a flowchart illustrating another example of the optical measurement method according to the embodiment 4. This flowchart assumes that the relationship described with FIGS. 19 and 20 is acquired in advance as calibration data. Hereinafter, each step in FIG. 20 will be described.

(FIG. 21: Step S211 to S214)

These steps are same as steps S181 to S184 in FIG. 18.

(FIG. 21: Step S215 to S216)

Defocuses and changes in detection signal amplitude are extracted for each cell (S215). The cell size is identified by referring to the calibration data exemplified in FIG. 20(c) using the acquired attenuation ratio of detection signal and defocus (S216).

(FIG. 21: Step S217)

The imaged detection signal and the measured cell size are arbitrarily selected and are shown on display, for example.

<Embodiment 4: Summary>

With the optical measurement method according to the embodiment 4, it is possible to non-invasively and directly measure the cell size and its distribution without adhering fluorescent molecules to the cell.

<Embodiment 5>

Figure 22:
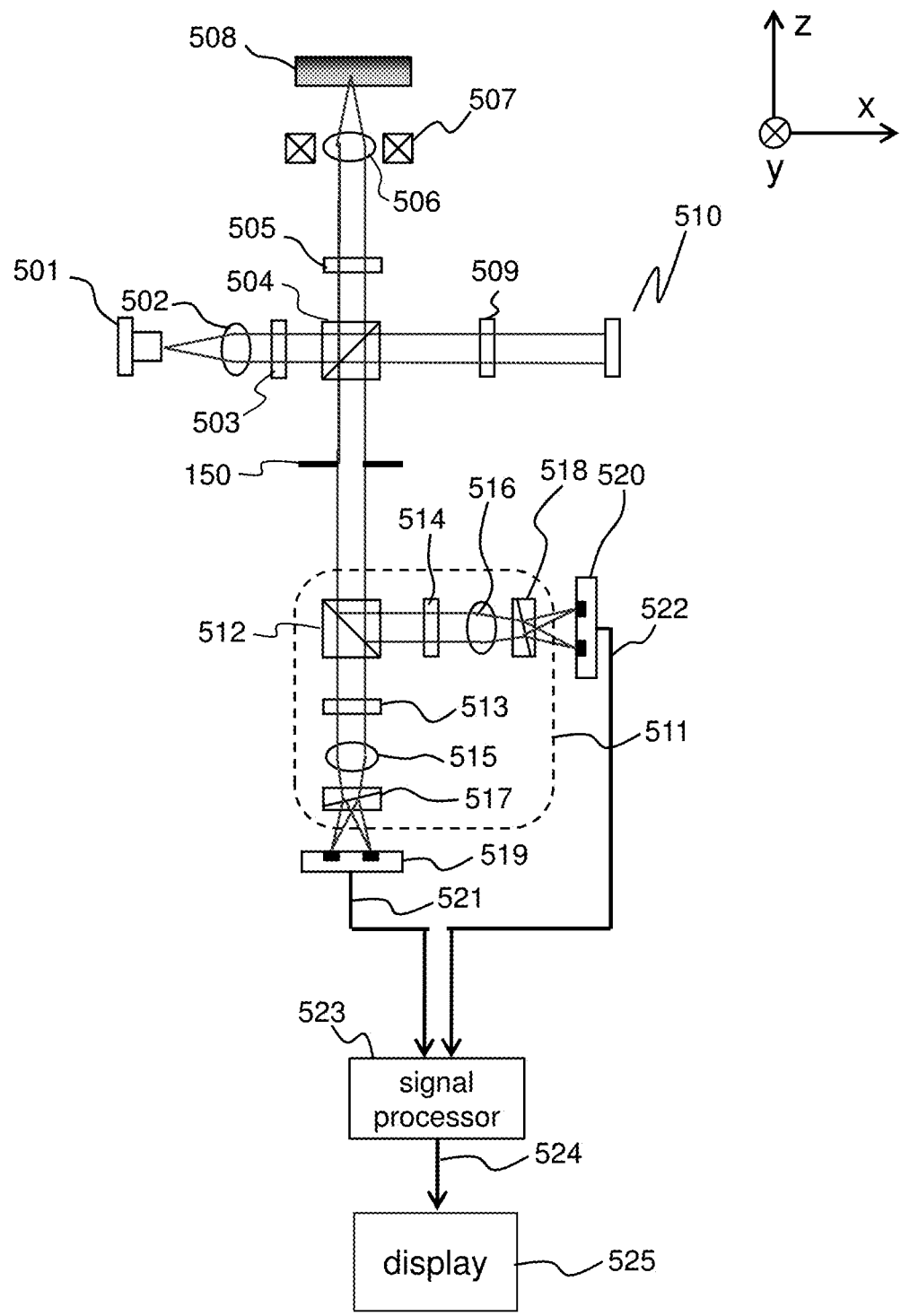
FIG. 22 is a schematic diagram illustrating a configuration of an optical measurement apparatus according to an embodiment 5.

FIG. 22 is a schematic diagram illustrating a configuration of an optical measurement apparatus according to an embodiment 5 of the present invention. The laser light emitted from the optical source 501 is converted into parallel light by the collimate lens 502. The polarization of the parallel light is rotated by the λ/2 plate 503 which optical axis is adjustable. The polarization beam splitter 504 divides the rotated light into signal light and reference light. The signal light reflected by the polarization beam splitter 504 transmits the λ/4 plate 505 which optical axis is approximately at 22.5 degree with respect to the horizontal direction, thereby converting the polarization from s polarization into circular polarization. Then the objective lens 506 focuses the signal light onto the specimen 508. The objective lens 506 may be scanned in xz directions by the objective lens actuator 507. The specimen 508 is movable in the y direction with a movable stage (not shown). With such configurations, the focus position of the objective lens is scanned in xyz directions with respect to the specimen.

The signal light reflected from the specimen transmits the objective lens 506. The λ/4 plate 505 converts the polarization of the signal light from circular polarization into p polarization. The signal light enters the polarization beam splitter 504. The reference light transmits the λ/4 plate 509 to convert the polarization from p polarization into circular polarization. The mirror 510 reflects the reference light. The λ/4 plate 509 converts the polarization of the reference light from circular polarization into s polarization. The reference light enters the polarization beam splitter 504. The polarization beam splitter 504 multiplexes the signal light with the reference light to produce multiplexed light. The multiplexed light is guided to the interference optical system 511 that comprises the half beam splitter 512, the λ/2 plate 513, the λ/4 plate 514, the detection lenses 515 and 516, and the Wollaston prisms 517 and 518. The multiplexed light entered into the interference optical system 511 is divided into transmitted light and reflected light.

The transmitted light transmits the λ/2 plate 513 which optical axis is approximately at 22.5 degree with respect to the horizontal direction. The transmitted light is focused by the detection lens 515. The Wollaston prism 517 separates polarization to produce first and second interference light which phases are different from each other by 180 degree. The first and second interference light are detected by the current differential optical detector 519. The optical detector 519 outputs the differential output signal 521 proportional to the intensity of the light.

The reflected light transmits the λ/2 plate 513 which optical axis is approximately at 22.5 degree with respect to the horizontal direction. The reflected light is focused by the detection lens 516. The Wollaston prism 518 separates polarization to produce third and fourth interference light which phases are different from each other by 180 degree. The phase of the third interference light is different from that of the first interference light by 90 degree. The third and fourth interference light are detected by the current differential optical detector 520. The optical detector 520 outputs the differential output signal 522 proportional to the intensity of the light.

The differential output signals 521 and 522 (hereinafter, referred to as I and Q) are inputted into the signal processor 523 to perform calculation. The display 525 displays detection signals that correspond to the reflected light from the specimen on the basis of the imaged signal 524, and displays the number and size of the cell measured in accordance with the embodiments 1 to 4, as image data and numerical data.

The virtual aperture 150 represents a virtual detection lens aperture in which the aperture of the detection lenses 515 and 518 are projected onto the signal light and the reference light multiplexed by the polarization beam splitter 504. The virtual aperture 150 is equivalent to the detection lens aperture mentioned above.

The theoretical background of the interference optical system 511 implements so-called phase diversity detection described in Patent Document 1. For the sake of simplicity, detailed description will be omitted here. The differential signals I and Q are described by Equations 8 and 9 below. xy represents the position of the virtual aperture 150. $E_{sig}$ represents a complex electric field amplitude of the signal light reflected from the specimen. $E_{ref}$ is a complex electric field amplitude of the reference signal. $\varphi_{sig}$ and $\varphi_{ref}$ represent phases of the signal light and the reference light corresponding to the optical path length from the optical source 501 to the virtual aperture 150, respectively. Integration means a correlation integration of the signal light and the reference light on the virtual aperture.

[Equation 8]

$$I = \int\int_A |E_{sig}(x, y)||E_{ref}(x, y)|\cos(\phi_{sig} - \phi_{ref})\,dx\,dy \qquad (8)$$

[Equation 9]

$$Q = \int\int_A |E_{sig}(x, y)||E_{ref}(x, y)|\sin(\phi_{sig} - \phi_{ref})\,dx\,dy \qquad (9)$$

The detection signal S may be calculated by Equation 10 below without using $\varphi_{sig}$ and $\varphi_{ref}$. It is obvious that Equation 10 is equivalent to Equation 3.

[Equation 10]

$$S = |E_{sig}|^2|E_{ref}|^2 = I^2 + Q^2 \qquad (10)$$

<Embodiment 6>

The two dimensional data Image(x, y) is generally acquired as digital values by converting the signal in Equation 1 with AD convertor using the optical system. In the embodiments 1 to 5, the two dimensional data Image(x, y) is acquired once. Thus if the gain is configured so that the output from the AD convertor does not saturate, sufficient resolution performance may not be available at portions with small signal intensity. In such cases, it is beneficial to effectively improve the resolution and SNR of the AD convertor by acquiring a plurality of the two dimensional data Image(x, y) and by integrating the acquired data. For example, if the AD convertor has 8 bits (256 levels), the two dimensional data Image(x, y) acquired 64 times and then integrated may be regarded as 14 bits (16384 levels) effectively. Then it is possible to acquire sufficient resolution and SNR. However, long measurement duration is required to acquire the two dimensional data 64 times consecutively. If the observed cell moves significantly due to Brownian motion, for example, the reliability of the integrated two dimensional data Image(x, y) will be lost. Thus an embodiment 6 of the present invention mainly describes a method for improving the effective resolution of the AD convertor.

Figure 23:
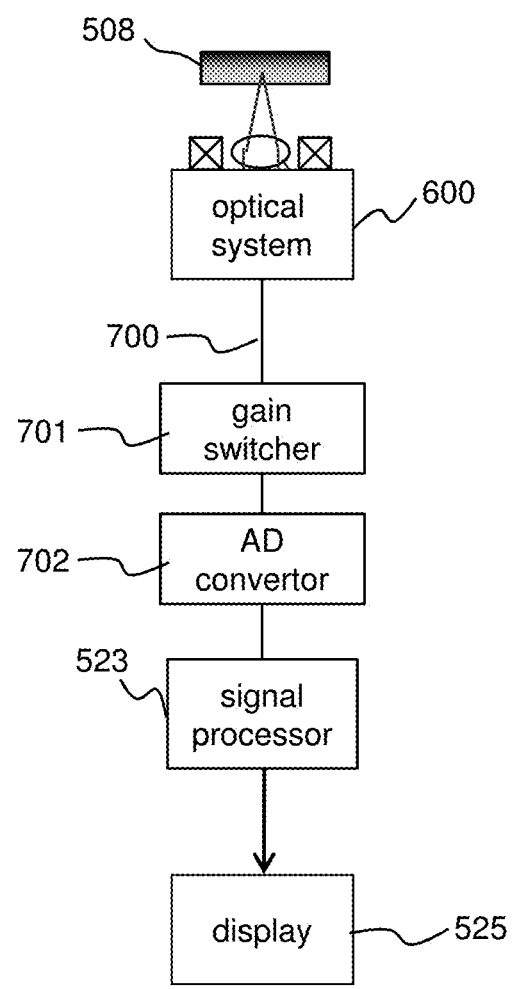
FIG. 23 is a schematic diagram illustrating a configuration of an optical measurement apparatus according to an embodiment 6.

FIG. 23 is a schematic diagram of an optical measurement apparatus according to the embodiment 6. The laser light emitted from the optical system 600 is irradiated onto the specimen 508. The reflected light is detected in the optical system 600 as the signal 700. The signal 700 is amplified by an amplification ratio specified by the gain switcher 701. The signal 700 is converted into digital values by the AD convertor 702. The signal 700 is movable in the y direction with a movable stage (not shown) by the signal processor 523. Such configurations acquire the two dimensional data Image(x, y). The display 525 shows the image.

Figure 24:
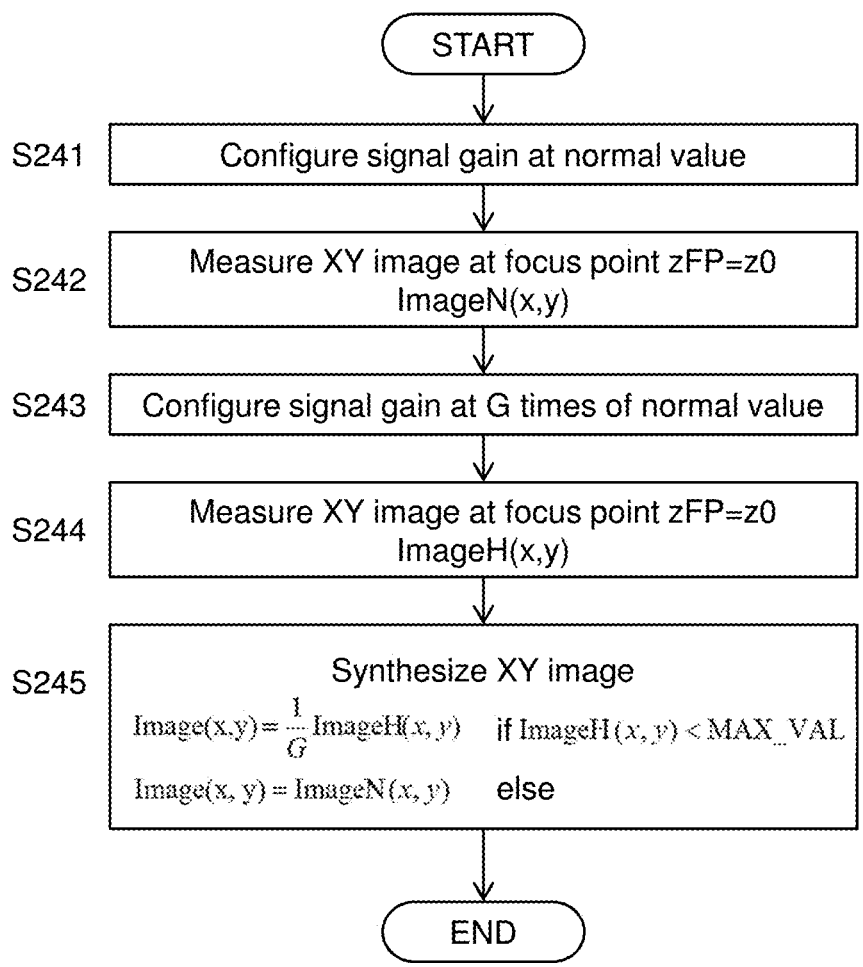
FIG. 24 is a flowchart describing an optical measurement method according to the embodiment 6.

FIG. 24 is a flowchart describing an optical measurement method according to the embodiment 6. Hereinafter, each step in FIG. 24 will be described.

(FIG. 24: Step S241)

The signal gain of the OCT apparatus is set at normal value. This corresponds to selecting the normal gain for the gain switcher 701 shown in FIG. 23.

(FIG. 24: Step S242)

The focus point of the objective lens of the OCT apparatus is set as zFP=z0. Two dimensional data ImageN(x, y), which is an observed image in the xy plane, is acquired using signal intensities acquired by scanning the detection light in the xy directions.

(FIG. 24: Step S243)

The signal gain of the OCT apparatus is set at G times of the normal value. This corresponds to selecting G times of the normal gain for the gain switcher 701 shown in FIG. 23.

(FIG. 24: Step S244)

The focus point of the objective lens of the OCT apparatus is again set as zFP=z0. Two dimensional data ImageH(x, y), which is an observed image in the xy plane, is acquired using signal intensities acquired by scanning the detection light in the xy directions.

(FIG. 24: Step S245)

Image(x, y), in which the resolution is improved at portions having small signal intensity, is synthesized from the acquired ImageN(x, y) and ImageH(x, y). Assuming that the maximum value of the output from the AD convertor is MAX_VAL, MAX_VAL=255 if the AD convertor has 8 bits. In this step, if ImageH(x, y)<MAX_VAL, i.e. if the data acquired at high gain is not saturated, Image(x, y) is calculated by Image(x, y)=1/G×ImageH(x, y) so that the gain of the data acquired with high gain is corrected. On the other hand, if the data acquired with high gain is saturated (ImageH(x, y)≥MAX_VAL), the data acquired with normal gain is employed and Image(x, y)=ImageN(x, y). This step is capable of acquiring the two dimensional data Image(x, y) by two times measurement with the resolution improved at portions with small signal levels.

By replacing the two dimensional data Image(x, y) acquired by this method with the data acquired in such as step S101 in FIG. 10 or step S142 in FIG. 14 or step S182 in FIG. 18, it is possible to measure size and position of the cell with high precision using the data with improved resolution. When implementing a control program using integers, for example, Image(x, y) may be calculated as Image(x, y)=ImageH(x, y) when not saturated and Image(x, y)=G×ImageN(x, y) when saturated.

<Variations of Present Invention>

The present invention is not limited to the embodiments, and various modified examples are included. The embodiments are described in detail to describe the present invention in an easily understood manner, and the embodiments are not necessarily limited to the embodiments that include all configurations described above. Part of the configuration of an embodiment can be replaced by the configuration of another embodiment. The configuration of an embodiment can be added to the configuration of another embodiment. Addition, deletion, and replacement of other configurations are also possible for part of the configurations of the embodiments.

The optical measurement method and apparatus measure number and size of cell using selectivity of OCT for reflected light in the focus point direction and using interference due to multiplex reflection from the object. As commonly known, similar selectivity in the focus point direction is available in confocal microscope. Thus the optical measurement method of the present invention may be applied to confocal microscope.

In the embodiments above, the focus point of the detection light is scanned. A same result is acquired by scanning the specimen. Thus any one may be arbitrarily selected depending on the device configuration.

The embodiment 4 focuses on measuring the cell size. The methods in the embodiments 1 to 3 may be performed along with the embodiment 4. This is capable of measuring number of cells simultaneously. The present invention may be applied when measuring size or number of specimen other than cells.

A part of or all of the signal processor 523 may be implemented with hardware by such as designing it with integrated circuits. Alternatively, the signal processor 523 may be implemented with software by a processor interpreting the program implementing each functionality and executing the software. Information, such as programs, tables, and files, for realizing the functions can be stored in a recording device, such as a memory, a hard disk, and an SSD (Solid State Drive), or in a recording medium, such as an IC card, an SD card, and a DVD.

DESCRIPTION OF SYMBOLS

150: virtual aperture
501: optical source
502: collimate lens
503, 513: λ/2 plate
504: polarization beam splitter
505, 509, 514: λ/4 plate
506: objective lens
507: objective lens actuator
508: specimen
510: mirror
511: interference optical system
512: half beam splitter
515, 516: detection lens
517, 518: Wollaston prism
519, 520: current differential optical detector
523: signal processor
525: display

What is claimed is:

1. An optical measurement method to measure a specimen having a size equal to or less than three times a size of an optical spot, comprising:
   focusing light at a plurality of predetermined focus points in an optical axis direction to generate the optical spot on the specimen;
   detecting, at each of the focus points, reflection light reflected from the specimen while scanning the optical spot across the specimen perpendicular to the optical axis direction; and
   acquiring a size of the specimen by referring to relationship data that describes a relationship between an intensity of the reflection light and the size of the specimen.

2. The optical measurement method according to claim 1,
   wherein a maximum signal value of the intensity of the reflection light is acquired at each of the focus points, and
   wherein the size of the specimen is acquired by referring to the relationship data using a half width of the maximum signal value of the intensity of the reflection light.

3. The optical measurement method according to claim 1,
wherein the relationship data describes a relationship among: a shifted amount representing an amount by which the focus point is shifted from a center of the specimen, an amount by which the intensity of the reflection light attenuates depending on the shifted amount, and the size of the specimen,
wherein an attenuation amount is acquired that represents an amount by which the intensity of the reflection light attenuates by shifting between the focus points in the optical axis direction, and
wherein the size of the specimen is acquired by referring to the relationship data using the attenuation amount and the amount by which each of the focus points is shifted when acquiring the attenuation amount.

4. An optical measurement apparatus that measures a specimen using an optical spot, the specimen having a size equal to or less than three times a size of the optical spot, comprising:

an optical source that irradiates laser light;

a lens that focuses the laser light onto a specimen;

a detector that detects reflection light reflected from the specimen; and a processor that is programmed to:

control the lens to focus the laser light at a plurality of predetermined focus points in an optical axis direction to generate the optical spot on the specimen, control the detector to detect, at each of the focus points, the reflection light reflected from the specimen while scanning the optical spot across the specimen perpendicular to the optical axis direction, and acquire a size of the specimen by referring to relationship data that describes a relationship between an intensity of the reflection light and the size of the specimen.

* * * * *